(12) United States Patent
Marchini et al.

(10) Patent No.: US 9,234,183 B2
(45) Date of Patent: *Jan. 12, 2016

(54) RETARGETING OF RAT PARVOVIRUS H-1PV TO CANCER CELLS THROUGH GENETIC ENGINEERING OF ITS CAPSID

(71) Applicant: DEUTSCHES KREBSFORSCHUNGSZENTRUM, Heidelberg (DE)

(72) Inventors: Antonio Marchini, Heidelberg (DE); Nazim El-Andaloussi, Heidelberg (DE); Jean Rommelaere, Heidelberg (DE); Barbara Leuchs, Heidelberg (DE); Xavier Allaume, Montreuil (FR)

(73) Assignee: DEUTSCHES KREBSFORSCHUNGZENTRUM, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/859,678

(22) Filed: Apr. 9, 2013

(65) Prior Publication Data

US 2013/0224154 A1 Aug. 29, 2013

Related U.S. Application Data

(63) Continuation of application No. PCT/EP2011/005229, filed on Oct. 18, 2011.

(60) Provisional application No. 61/405,525, filed on Oct. 21, 2010.

(51) Int. Cl.
| | |
|---|---|
| C12N 7/00 | (2006.01) |
| C12N 15/00 | (2006.01) |
| A61K 35/768 | (2015.01) |
| C07K 14/005 | (2006.01) |

(52) U.S. Cl.
CPC ................ *C12N 7/00* (2013.01); *A61K 35/768* (2013.01); *C07K 14/005* (2013.01); *C12N 2750/14321* (2013.01); *C12N 2750/14322* (2013.01); *C12N 2750/14332* (2013.01)

(58) Field of Classification Search
None
See application file for complete search history.

(56) References Cited

U.S. PATENT DOCUMENTS

2004/0220124 A1 11/2004 Rommelaere

FOREIGN PATENT DOCUMENTS

| WO | WO 03/054197 A2 | 7/2003 |
| WO | WO 2011/138053 A2 | 11/2011 |

OTHER PUBLICATIONS

Girod et al. Genetic capsid modifications allow efficient re-targeting of adeno-associated virus type 2. Nat Med. Sep. 1999;5(9):1052-6.*
International Search Report and Written Opinion of PCT Application No. PCT/EP2011/005229 with a mailing date of May 7, 2012.
Allaume X. et al.; "Retargeting of Rat Parvovirus H-1PV to Cancer Cells Through Genetic Engineering of the Viral Capsid"; Journal of Virology, The American Society for Microbiology, US; p. 43PP (Jan. 1, 2012).
Assa-Munt, et al.; "Solution Structures and Integrin Binding Activities of an RGD Peptide with Two Isomers"; Biochemistry; vol. 40, No. 8, pp. 2373-2378 (2001).
Calle, et al.; "Parvovirus H-1 Infection of Human Glioma Cells Leads to Complete Viral Replication and Efficient Cell Killing"; Int. J. Cancer; vol. 109, pp. 76-84 (2004).
Candace, et al.; "Membrane-Associated Heparan Sulfate Proteoglycan is a Receptor for Adeno-Associated Virus Type 2 Virions"; Journal of Virology; vol. 72, No. 2, pp. 1438-1445 (Feb. 1998).
Candace, et al.; "$\alpha v \beta 5$ Integrin: A Co-Receptor for Adeno-Associated Virus Type 2 Infection"; Nature Medicine; vol. 5, No. 1, pp. 78-82 (Jan. 1999).
Coughlan, et al.; "In Vivo Retargeting of Adenovirus Type 5 to $\alpha v \beta 6$ Integrin Results in Reduced Hepatotoxicity and Improved Tumor Uptake Following Systemic Delivery"; Journal of Virology; vol. 83, No. 13, pp. 6416-6428 (Jul. 2009).
Etingov, et al.; "An Extension of the Minute Virus of Mice Tissue Tropism"; Virology; vol. 379, pp. 245-255 (Aug. 5, 2008).
Girod, et al.; "Genetic Capsid Modifications Allow Efficient Re-Targeting of Adeno-Associated Virus Type 2"; Nature Medicine; vol. 5, No. 9, pp. 1052-1056 (Sep. 1999).
Gonzalez, et al.; "Increased Gene Transfer in Acute Myeloid Leukemic Cells by an Adenovirus Vector Containing a Modified Fiber Protein"; Gene Therapy; vol. 6, pp. 314-320 (1999).
Hueffer, et al.; "Parvovirus Host Range, Cell Tropism and Evolution"; Current Opinion in Microbiology; vol. 6, pp. 392-398 (2003).
Kontou, et al.; "Structural Determinants of Tissue Tropism and In Vivo Pathogenicity for the Parvovirus Minute Virus of Mice"; Journal of Virology; vol. 79, No. 17, pp. 10931-10943 (Sep. 2005).
Krasnykh, et al.; "Characterization of an Adenovirus Vector Containing a Heterologous Peptide Epitope in the Hi Loop of the Fiber Knob"; Journal of Virology; vol. 72, No. 3, pp. 1844-1852 (Mar. 1998).
Kruger, et al.; "Augmented Transgene Expression in Transformed Cells Using a Parvoviral Hybrid Vector"; Cancer Gene Therapy; vol. 15, pp. 252-267 (Jan. 18, 2008).
Lopez-Bueno, et al.; "Evolution to Pathogenicity of the Parvovirus Minute Virus of Mice in Immunodeficient Mice Involves Genetic Heterogeneity at the Capsid Domain That Determines Tropism"; Journal of Virology; vol. 82, No. 3, pp. 1195-1203 (Feb. 2008).
Lopez-Bueno, et al.; "Host-Selected Amino Acid Changes at the Sialic Acid Binding Pocket of the Parvovirus Capsid Modulate Cell Binding Affinity and Determine Virulence"; Journal of Virology; vol. 80, No. 3, pp. 1563-1573 (Jan. 13, 2006).
Malerba, et al.; "Replicating Parvoviruses That Target Colon Cancer Cells"; Journal of Virology; vol. 77, No. 12, pp. 6683-6691 (Jun. 2003).

(Continued)

*Primary Examiner* — Zachariah Lucas
*Assistant Examiner* — Nick Zou
(74) *Attorney, Agent, or Firm* — Perkins Coie LLP; Viola T. Kung

(57) ABSTRACT

Described is a parvovirus, in particular a H-1PV, that can be genetically retargeted through modification of its capsid, which is useful in cancer therapy.

10 Claims, 17 Drawing Sheets

(56) References Cited

OTHER PUBLICATIONS

Michelfelder, et al.; "Successful Expansion but Not Complete Restriction of Tropism of Adeno-Associated Virus by in Vivo Biopanning of Random Virus Display Peptide Libraries"; PLoS ONE; vol. 4, Issue 4, e5122 (Apr. 9, 2009).

Muller, et al.; "Random Peptide Libraries Displayed on Adeno-Associated Virus to Select for Targeted Gene Therapy Vectors"; Nature Biotechnology; vol. 21, No. 9, pp. 1040-1046 (Aug. 3, 2003).

Nam et al.; "Identification of the Sialic Acid Structures Recognized by Minute Virus of Mice and the Role of Binding Affinity of Virulence Adaption"; The Journal of Biological Chemistry; vol. 281, No. 35, pp. 25670-25677 (Sep. 1, 2006).

Nia, et al.; "In Vivo Bioluminescence Tumor Imaging of RGD Peptide-modified Adenoviral Vector Encoding Firefly Luciferase Reporter Gene"; Molecular Imaging and Biology; vol. 9, pp. 126-134 (Feb. 13, 2007).

Parker, et al.; "Canine and Feline Parvoviruses Can Use Human or Feline Transferrin Receptors to Bind, Enter, and Infect Cells"; Journal of Virology; vol. 75, No. 8, pp. 3896-3902 (Apr. 2001).

Pasquale, et al.; "Identification of PDGFR as a Receptor for AAV-5 Transduction"; Nature Medicine; vol. 9, No. 10, pp. 1306-1312 (Oct. 2003).

Qing, et al.; "Human Fibroblast Growth Factor Receptor 1 is a Co-Receptor for Infection by Adeno-Associated Virus 2"; Nature Medicine; vol. 5, No. 1, pp. 71-77 (Jan. 1999).

Rommelaere J. et al.; "Oncolytic Parvoviruses as Cancer Therapeutics"; Cytokine and Growth Factor Reviews, Elsevier Ltd., GB; vol. 21, No. 203, pp. 185-195 (Apr. 1, 2010).

Rubio et al.; "Virulent Variants Emerging in Mice Infected with the Apathogenic Prototype Strain of the Parvovirus Minute Virus of Mice Exhibit a Capsid with Low Avidity for a Primary Receptor"; Journal of Virology; vol. 79, No. 17, pp. 11280-11290 (Sep. 2005).

Weigel-Kelley, et al.; "$\alpha 5\beta 1$ Integrin as a Cellular Coreceptor for Human Parvovirus B19: Requirement of Functional Activation of $\beta 31$ Integrin for Viral Entry"; Blood, American Society of Hematology; vol. 102, No. 12, pp. 3927-3933 (Aug. 7, 2003).

Calle et al.: Parvovirus H-1 Infection of Human Glioma Cells Leads to Complete Viral Replication and Efficient Cell Killing. Int. J. Cancer, 2004, vol. 109, pp. 76-84.

Bar et al.: Vesicular Egress of Non-Enveloped Lytic Parvoviruses. PLOS Pathogens, 2008, vol. 4, No. 8, pp. 1-11.

Zhi et al.: Molecular and Functional Analyses of a Human Parvovirus B19 Infectious Clone Demonstrates Essential Roles for NS1, VP1, and the 11-Kilodalton Protein in Virus Replication and Infectivity. Journal of Virology, Jun. 2006, p. 5941-5950.

\* cited by examiner

*In silico* modelling of H-1PV VP2

In silico modelling of H-1PV viral capsid

**Sequence alignment of H-1PV and MVM VP2 "dimple" region:
identification of putative aminoacids involved in sialic acid binding**

Sialic acid is involved in viral-cell membrane recognition and viral entry

Virus binding and entry assays

Fig. 5A Electron microscopy
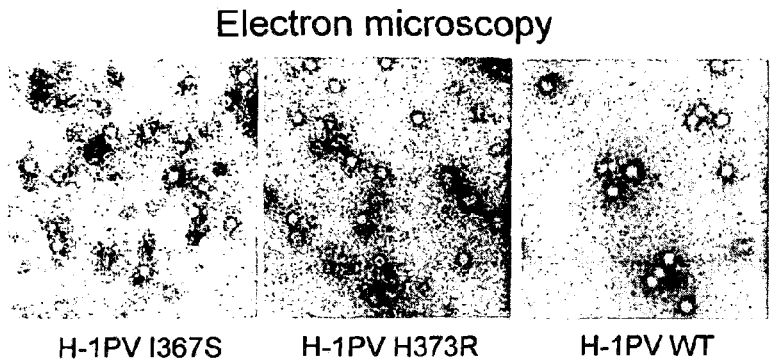
H-1PV I367S    H-1PV H373R    H-1PV WT
Fig. 5B Binding entry assays
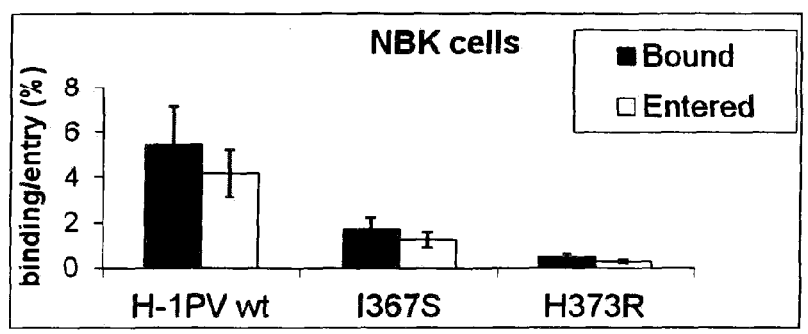
Fig. 5C Infection unit and plaque assays
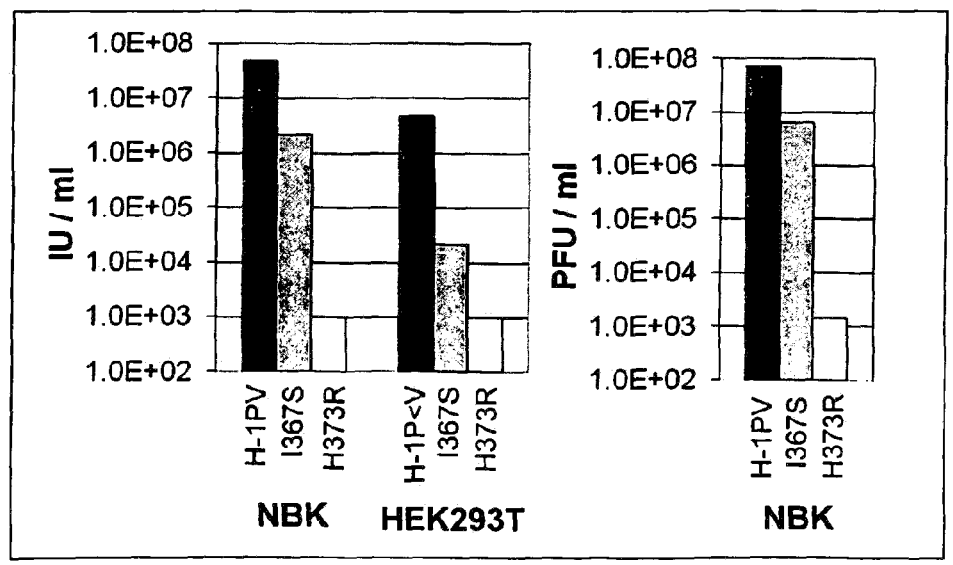

Fig. 5D  Virus production via transfection
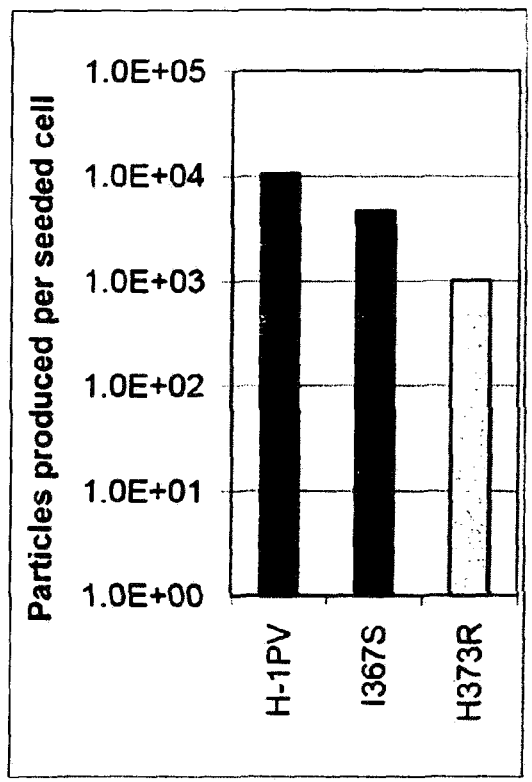
Fig. 5E  Binding entry assays
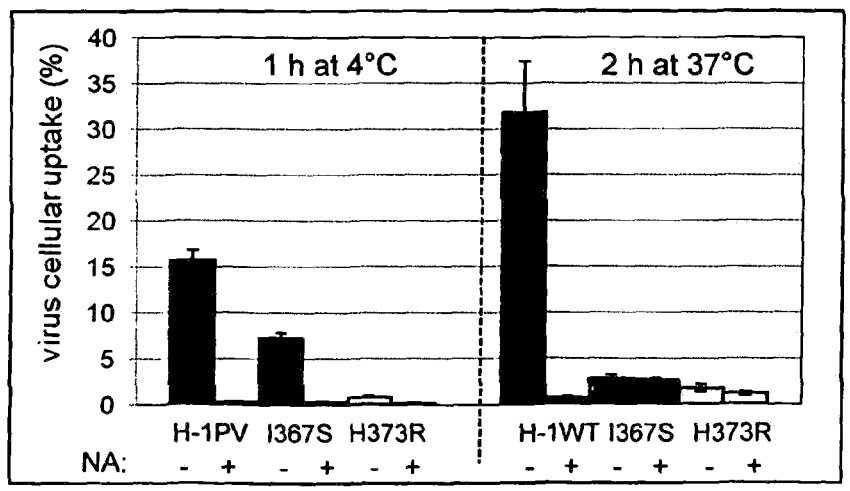

Fig. 5F Infection unit assay
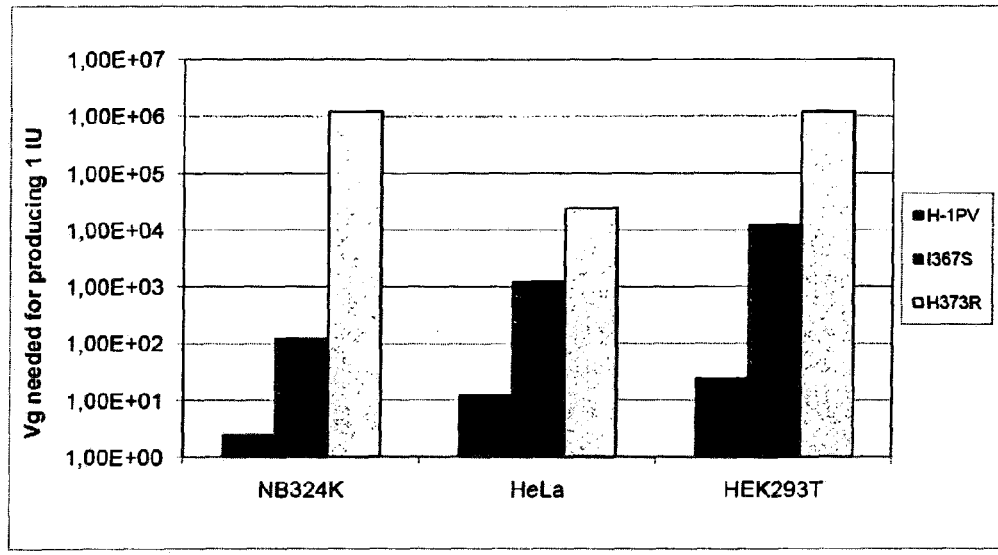
Fig. 5G Plaque assay
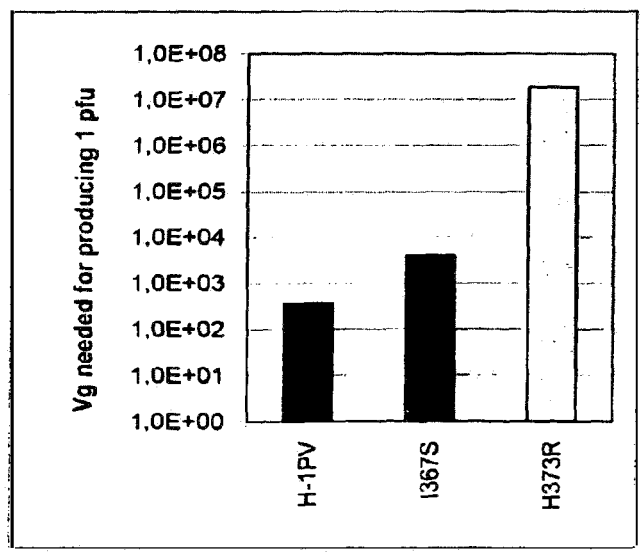

Analysis of the model for the identification of putative insertional sites
A
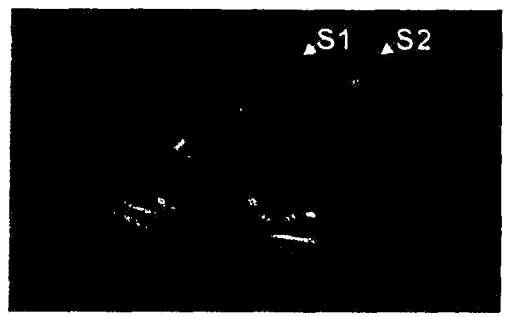
B
Modelling of RGD-4C into S1 and S2
C
Fig. 6

Re-targeting H-1PV: insertion of RGD-4C peptide

Electron microscopy

H-1PV-H373R-RGD-4C
(H-1RGD)

Virus production via transfection

Fig. 7C   FACS analysis for integrin content
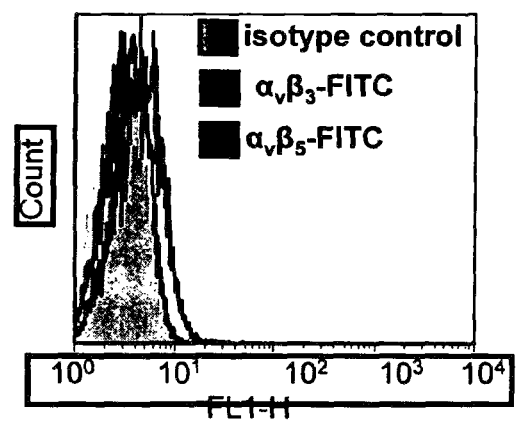
Fig. 7D   Infection unit assay
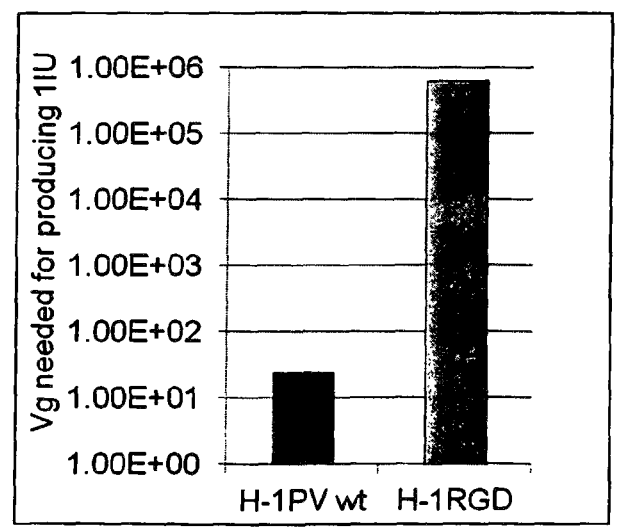

H-1PV-I367S

H-1PV-H373R-RGD-4C

Re-targeting H-1PV: insertion of RGD-4C peptide confers a new tropism to the virus

Fig. 11A          FACS analysis for integrin content

■ isotype control   ■ $\alpha_v\beta_3$-FITC   ■ $\alpha_v\beta_5$-FITC

Fig. 11B  Binding entry assays

Re-targeting H-1PV: insertion of RGD-4C peptide does not impair the capacity of the virus to kill cancer cells cell viability assay

RETARGETING OF RAT PARVOVIRUS H-1PV TO CANCER CELLS THROUGH GENETIC ENGINEERING OF ITS CAPSID

This application is a continuation of PCT/EP2011/005229, filed Oct. 18, 2011; which claims the priority of U.S. Provisional Application No. 61/405,525, filed Oct. 21, 2010. The contents of the above-identified applications are incorporated herein by reference in their entireties.

This invention provides a parvovirus, in particular a H-1PV, that can be genetically retargeted through modification of its capsid, which is useful in cancer therapy.

Parvoviruses (PV) are small, non-enveloped, single-stranded DNA viruses that infect a wide variety of animal species, from insects to humans (1). Since the original observation that parvovirus minute virus of mice (MVM) can kill transformed human cells (2), other autonomous rodent parvovirus, such as rat H-1PV, were described to have oncolytic and oncosuppressive activities in various cell culture and animal models (3, 4) while being non-pathogenic for humans.

The antineoplastic activity of PVs is not due to better virus uptake by transformed cells but to a more efficient viral replication in these cells. This is mainly due to the fact that PV's replication and viral gene expression are dependent on cellular factors such as E2F, CREB, ATF, cyclin A (5) and others, all known to be upregulated in cancer cells. Moreover, PVs did not evolve strategies capable to counteract cellular antiviral defense mechanisms (6). As cancer cells are often defective in these antiviral pathways, they provide a more favorable environment for the viral life cycle.

In addition to its antineoplastic activities, another positive aspect of using rodent PVs in cancer therapy is that generally humans have been not previously exposed to parvovirus infection and this avoids the problem of a rapid virus elimination resulting from preexisting antiviral immunity (7). This places PVs in a better position respect to other vectors used in cancer therapy which are based on human pathogens (e.g. adenovirus, HSV, VSV etc.). Altogether, these properties make these viruses very attractive as anticancer agents.

Although the anticancer potential of H-1PV is supported by a large set of preclinical studies, efficacy can be expected to be a limiting factor in clinical applications. One major limitation is the fact that PVs can still enter normal cells. The uptake of the virus by non-tumour cells sequesters a significant portion of the administered viral dose away from the tumor target. Targeting PV entry to tumor cells would thus increase the efficacy of parvovirus-based treatments and provide additional safety against possible side-effects on normal cells.

Several attempts have been made to modify the natural cell entry of PVs, based on adaptation of the natural strains to new cell types in cell culture (8) or in vivo (9, 10) experiments. These approaches however, lack predictability, are limited to previously semi-permissive cell lines and already existing tropisms of the virus. Alternatively, PVs with altered tropism have also been generated by replacing the whole capsid with the one of a related virus (11). However, this strategy has the limitation that the modification is not heritable and that progeny viruses do not maintain the same retargeting abilities of the initial viral dose. An approach to increase the oncotropism of the virus would be to genetically retarget the cell entry of the virus to cancer-cell specific receptors. This strategy has proved successful in retargeting other non-enveloped viruses for gene therapy or onco-therapeutic purposes, for instance with the related adeno-associated virus (AAV) (12-15), or adenovirus (16-18), but attempts to retarget members of the autonomous parvovirus subgroup have been not yet reported.

Thus, it is the object of the present invention to provide retargeted parvoviruses that increase the efficacy of parvovirus-based treatments and provide additional safety against possible side-effects on normal cells.

According to the invention this is achieved by the subject matters defined in the claims. Thus, the present invention provides genetically reprogrammed H-1PV in order to improve its affinity for human tumour cells. By analogy with the resolved crystal structure of the closely related parvovirus MVM, an in silico 3D model of the H-1PV wild-type capsid was developed. Based on this model, amino-acids for cell membrane recognition and virus entry were identified at the level of the twofold axis of symmetry of the capsid, within the so-called "dimple" region. In situ mutagenesis of these residues significantly reduced the binding and entry of H-1PV into permissive cells. Then, the entry-deficient viral capsid was engineered and inserted at the level of its threefold axis spike, a cyclic 4C-RGD peptide. This peptide binds $\alpha v \beta 5$ and $\alpha v \beta 5$ integrins, known to be over-expressed in cancer cells and growing blood vessels. Insertion of the peptide rescued viral infectivity towards cells over-expressing $\alpha v \beta 5$ integrins that were efficiently killed by the reengineered virus.

An embodiment of the invention relates to rat H-1PV which infects and kills numerous human tumour cell lines e.g. of brain (19), colon (20), cervix (21), mammary (22, 23) origin and that is currently under evaluation in phase I and II clinical trials for the treatment of patients with recurrent glioblastoma multiforme (5). It has been shown that depending on the cell type and experimental conditions, H-1PV has the ability to induce different cell death pathways in cancer cells, ranging from necrosis (24), apoptosis (25-28) and lysosomal dependent cell death (29), while sparing non-transformed cells. We have reported the capacity of the virus to induce oxidative stress in cancer cells, leading to DNA damage, cell cycle arrest and apoptosis. These effects are mediated by the non-structural NS1 protein (28).

The method of the present invention consists of two steps. First, the virus natural tropism to prevent it from entering its originally permissive cells is abrogated. This is achievable by modifying the capsid residues involved in cell recognition and binding. Second, the virus is retargeted specifically to cancer cells by grafting into the viral capsid a foreign peptide with high affinity for receptors that are only, or preferentially, expressed in cancer cells. This step requires the identification of a position within the viral capsid, which tolerates the insertion of the peptide and allows for the retargeting of the virus while maintaining its oncolytic potential. Both steps are very challenging due to the structural constrains that the icosahedral capsid of the virus imposes; indeed changes in the capsid are often incompatible with efficient particle assembly. The retargeting steps also imply a precise knowledge of the capsid structural and functional elements, and in particular the region(s) involved in binding to one or several specific cell receptors, all of which have so far not been studied in the case of H-1PV.

The capsid of the Parvoviridae family consists of 60 copies of two to three nested polypeptide sequences assembled in a T=1 icosahedral symmetry (30). In the case of H-1PV, the capsomers VP-1 and VP-2 are encoded by alternatively spliced transcripts, sharing a C-terminal core sequence but having N-terminal extensions of different lengths. The outer architecture of classical parvovirus capsid shows a "spike"-like protrusion at the threefold axis of symmetry, a depression, called the "dimple", at the twofold axis, and a pore connecting the inside of the virion to the exterior of the particle at the fivefold axis of symmetry (30). The cellular receptors for members of the parvovirus family have been described for the feline (FPV) serotype and its canine-tropic variant CPV, in which cell entry is mediated by binding to the transferrin receptor (TfR) (31). Different serotypes of AAV enter via binding to heparin sulfate proteoglycans (32), $\alpha_v\beta_5$ integrins (33), fibroblast growth factor receptor (34), or platelet-derived growth factor receptor alpha (35). Globoside (Gb4Cer) (36), Ku80 autoantigen (37) and $\alpha_v\beta_1$ integrin (38) have been identified as cell receptors/coreceptors for the human pathogen B19. Yet most of the cell receptors for the members of this family remain unknown, in particular for the rodent parvoviruses (39). It is known that the binding to sialic acid is required for cell surface receptor recognition by MVM, since both cell membrane attachment and infection are neuraminidase sensitive. The X-ray crystal structure of MVMp capsids soaked with sialic acid (N-acetyl neuraminic acid) reveals that the sugar is positioned within the dimple recess surrounding the icosahedral twofold symmetry axis of the viral capsid, immediately adjacent to residues I362 and K368. Point-mutations of these residues result in lower affinity for the sialic acid component of the cell receptor (10, 40-42).

Among the peptides suitable for specific tumour-targeting of chemicals, diagnostic tools or viral anti-cancerous agents, one of the most extensively studied is the Arg-Gly-Asp (RGD) peptide (43-46). The RGD sequence can be found in many extracellular matrix (ECM) proteins e.g. fibronectin, vitronectin etc. and is responsible for the binding of these ECM proteins to their cellular receptors (47). The RGD peptide, particularly in its cyclic form, CDCRGDCFC (termed RGD-4C), binds strongly to $\alpha_v\beta_3$ and $\alpha_v\beta_5$ integrins (48, 49) which are typically over-expressed in cancer cells and angiogenic blood vessels (50, 51). The RGD-4C/integrins interaction has been successfully exploited for retargeting adenoviruses (52-54) and adeno-associated viruses (13) to cancer cells.

In summary, the present invention provides a genetically reprogramed H-1PV entry through modification of its capsid. In the absence of structural data, we modeled the H-1PV capsid based on its homology with the capsid of the highly related MVM whose crystal structure has been resolved. The model allowed the identification of candidate amino acids involved in cellular recognition and entry. Mutation of these residues abrogates cellular entry and the insertion of a protruding RGD-4C peptide at the level of the capsid's threefold axis spike rescued virus infectivity and cellular killing, conferring a new cancer specific tropism to the engineered virus. In conclusion, this invention paves the way for a more efficient and safer use of H-1PV in clinical applications.

The generation of a genetically reprogrammed H-1PV according to the invention is described in the examples below. The method pursued consisted of four inventive steps:

1) In Silico Modelling of Parvovirus H-1PV Capsid.

This was important for acquiring a precise knowledge of structural and functional elements of the capsid, e.g. aminoacids involved in cell membrane recognition and entry and identification of places tollerating the insertion of retargeting peptides.

2) The Discovery that Sialic Acid is Required for the Cell Membrane Binding and Entry of H-1PV.

This was demonstrated by showing that virus infection is sensitive to neurominidase, a compound known to cleave sialic acid from the cell surface. Pretreatment with neurominidase dramatically decreased the capacities of H-1 to bind and enter NBK and HeLa cells (two highly permissive cell lines for H-1), providing evidence that sialic acid is an important component of the virus receptor(s).

3) Detargeting Step.

This step abrogated the parvovirus natural tropism preventing viral entry into originally permissive cells. This step consisted in mutagenizing the viral genome (capsid proteins encoding region) within the positions encoding for the amino acids involved in the binding to sialic acid (I367 and H373 of the VP2 protein corresponding to I509 and H515 in VP1 protein respectively). Candidate amino acids involved in sialic acid recognition were found on the basis of our structural model and functional homology with the related autonomous parvovirus MVM. In particular, modification of residue 373 (H→R) strongly impaired the capacity of the virus to bind and enter the cells (more than 90% reduction when compared with H-1 wt).

4) Retargeting Step.

The retargeting was achieved by inserting into the viral capsid a RGD-4C retargeting peptide that has high affinity for $\alpha v\beta 3$ and $\alpha v\beta 5$ integrins (48, 49), typically over-expressed in cancer cells and angiogenic blood vessels (50, 51). This step required the identification of a position within the viral capsid, tolerating the insertion of the peptide, maintaining its retargeting characteristics without affecting the oncolytic potential of the virus. This position into the viral genome was identified thanks to our model, and corresponds to the nucleotides encoding for A441 of the VP2 capsid protein (corresponding to A583 of the VP1 protein). Grafting of the RGD-4C peptide within this position rescued viral infectivity of the entry deficient mutant. The novel virus is able to enter the cells through an alternative route than the one used by wild type virus, which does not rely on sialic acid.

The superimposition of the ribbon diagrams of H-1 (red) and MVMpb (blue) VP2, illustrating β-strand, helical and loop regions. The position of the conserved β-strands, βB to βI, helix αA, the first N-terminal residue (G38 for H-1PV corresponding to G39 for MVM) and the last C-terminus residues (Y592 for H-1PV corresponding to Y587 for MVM) are indicated. The approximate position of the icosahedral 2-, 3-, and 5-fold axes are shown as filled oval, triangle, and pentagon, respectively. This figure was generated using the CPHmodels 3.0 Server at the Center for Biological Sequence Analysis of the Technical University of Denmark DTU as described in the Materials and Methods section.

Figure 2:
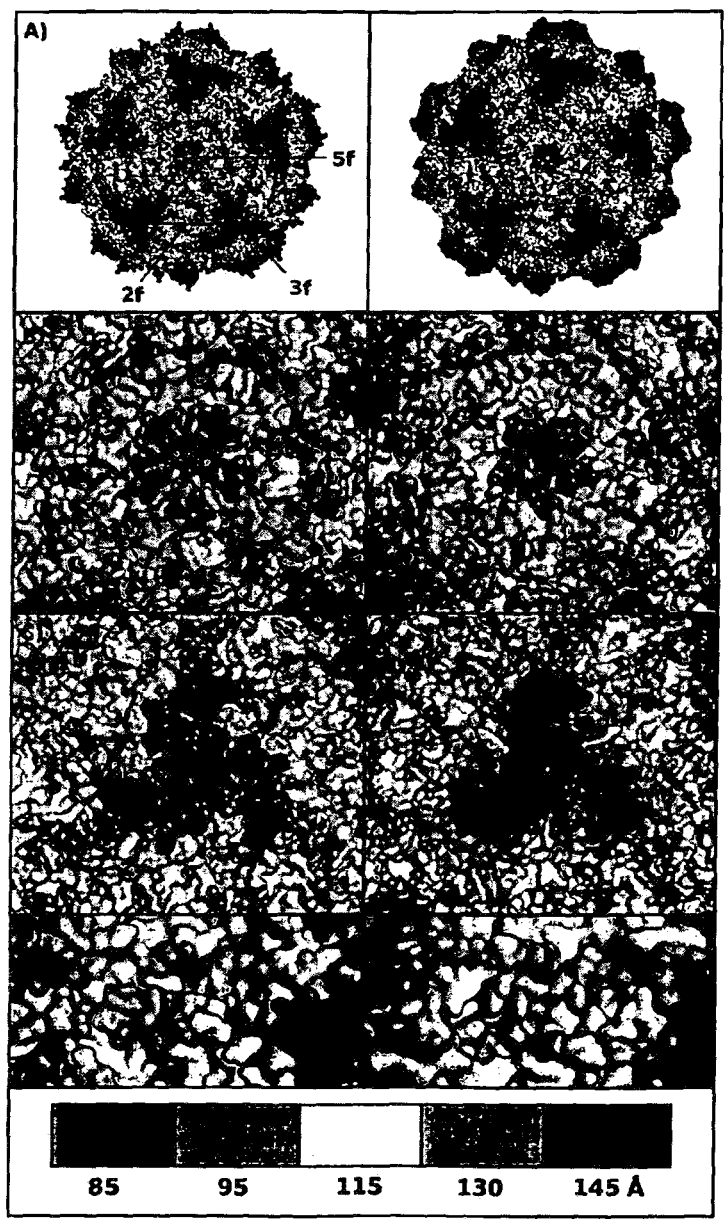

FIG. 2: In silico model of H-1 and MVMpb parvovirus capsids (A) The capsid of H-1PV (left) was modelled taking as a template the available crystal structure model of the MVMpb (right) capsid using the PyMol software as indicated in the Materials and Methods section. The approximate position of icosahedral fivefold (5f), threefold (3f), and twofold (2f) axes of symmetry are shown for a viral asymmetric unit.

(B to D) Close-up views of the H-1 (left) and MVMpb (right) capsid surfaces at the fivefold (B), threefold (C), and twofold (D) icosahedral axes. The panel at the bottom depicts the color range (in Å) for the depth-cued distances from the viral center of the particles. Color coding of the particles was generated by a home-developed algorithm and images generated with the PyMol software as indicated in the Materials and Methods section.

Figure 3:
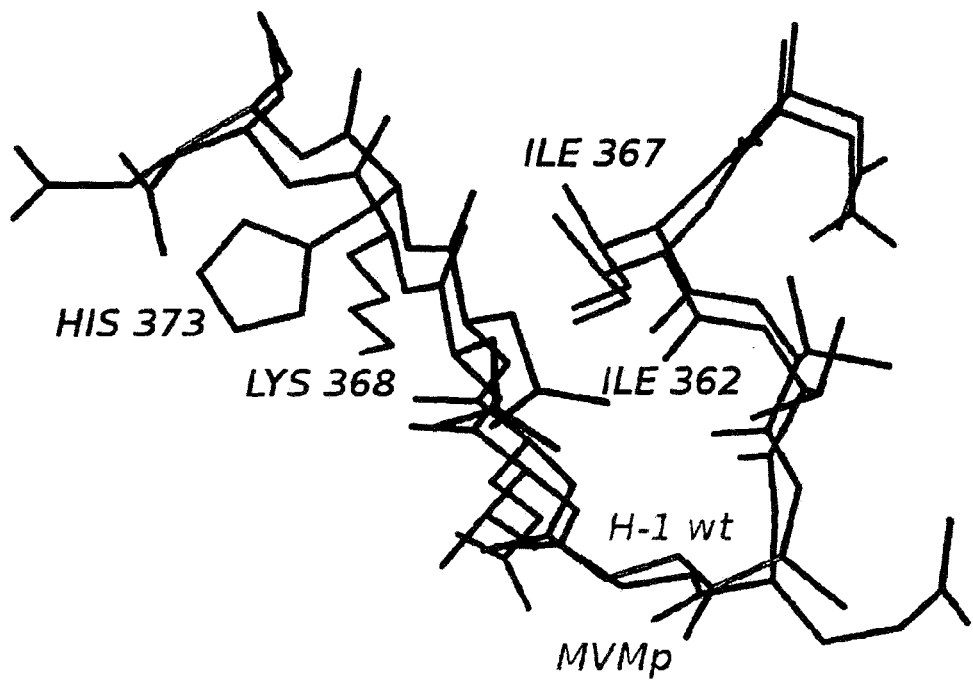

FIG. 3: 3D structural alignment of H-1PV and MVMpb VP2s and identification of potential H-1PV sialic acid binding residues MVMpb VP2 from model 1Z14 (pink) and H-1 wt VP2 model (light blue) were aligned using the "align" routine implemented in the PyMol software. Only the region 361-369, containing amino acids Ile-362 and Lys-368 (displayed in deep blue), known to bind to sialic acid in MVM, is represented. The corresponding residues Ile-367 and His-373 in H-1 wt VP2 sequence 366-374 are displayed in red.

Figure 4:
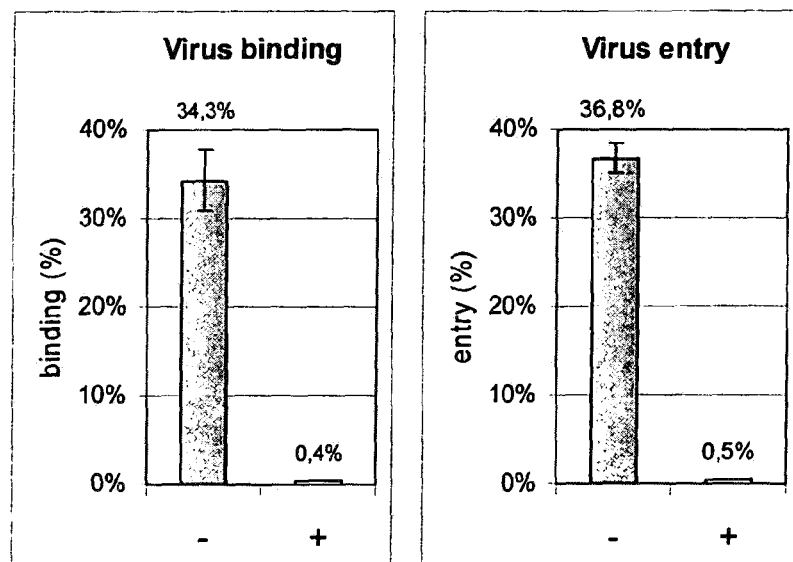

FIG. 4: Sialic acid is involved in H1PV cell membrane recognition and entry

HeLa cells were cultured in 24-well plates, at a density of $10^5$ cells per well, and treated (+) or not (−) with 0.1 U/ml Neuraminidase for 3 h at 37° C. Cellular medium was then replaced by medium containing purified H-1PV. The infection step was carried out for 1 h at 4° C. for the virus binding assay and for 2 h at 37° C. for the virus entry assay. Cells were washed with 500 µl of PBS, then treated with 100 µL of trypsin [0.25% (binding) and 0.05% (entry)] and the reaction was stopped with 200 µL of complete medium. Cells were then harvested and viral particles extracted by lysing the cells with three snap freeze/thaw cycles. Viral DNA was purified from inputs and cell fractions using the QiaAmp MinElute Virus kit and then quantified using a parvovirus specific qPCR as described in Example 1. The results are presented as percentage of particles taken up by the cells relative to input virus. Numbers on top of columns and bars indicate average values and standard deviations from triplicate measurements, respectively.

FIG. 5: Detargeting H-1PV by I367S and H373R substitution.

(A) Electron microscopy analysis showing that the mutations introduced did not change the capacity of the VP proteins to form capsids.

(B) Binding/entry assay. NBK cells were grown in a 48 well plate. After 24 h, cells were infected with H-1PV wild type (wt) or H-1PV mutants (I367S and H373R) at the concentration of $10^4$ Vg/cell and incubated at 4° C. for 30 min (viral binding assay). Plates were then washed with serum free medium in order to remove unbound viral particles, and then incubated at 37° C. for additional 2 h (viral entry assay). After washing with 500 µL of PBS, cells were treated with 100 µL of trypsin 0.05% (Invitrogen, Germany) before the reaction was stopped by adding 100 µL of complete medium. Cells were then collected and treated as described in the legend for FIG. 4.

(C) Virus infectivity was assessed in NBK and HEK 293T indicator cells by infection unit and plaque assays as described in Example 1. IU, infection units (determined by in situ hybridization); PFU, plaque-forming units (determined by plaque assay). All values were normalized for viral input.

(D) Virus production. HEK293T cells were transfected with the indicated viral plasmids and grown for a total of 5 days. After benzonase treatment for digesting cellular DNA and non-encapsidated viral DNA, crude cell extracts were analyzed for the presence of full virions. Viral particles were determined by PCR quantification of encapsidated viral genomes. Columns represent the numbers of produced particles divided by the number of cells seeded prior DNA transfection.

(E) Uptake. HeLa cells were infected with H-1PV wild-type (H-1PV) or H-1PV mutants (I367S and H373R) for the time and at the temperature indicated. Cellular uptake was determined as described above.

(F) Infectivity. Wild-type and mutant H-1PV were tested for their capacity to form infectious centers in NB324K, HeLa and HEK293T indicator cells as described in Example 1. IU, infectious units. Values indicate the number of purified particles (expressed as encapsidated Vg) that need to be inoculated per cell in order to produce 1 IU.

(G) Plaque formation. Wild-type and mutant H-1PV were tested for their capacity to form plaques in NB324K indicator cells. PFU, plaque-forming units. Values represent the amounts of purified particles (expressed as encapsidated Vg per cell) needed for producing 1 plaque.

FIG. 6: Model-based search for candidate sites tolerating the insertion of retargeting peptides in the H-1PV capsid.

(A) VP2 structural model reveals the presence of loops exposed at the surface of the viral capsid. Screening of these loops for hydrophilic regions, better suitable for the peptide insertion, reveals two optimal places, S1 and S2 indicated in white. The amino acid R373, which was substituted for H373 to detarget H-1PV, is shown in red.

(B) 3D model of the viral capsid (three capsomers are indicated) showing the position of the S2 site (in green) that was selected as the most favourable position for the insertion of the retargeting peptide.

(C) Simulation of the insertion of the RGD-4C peptide (CDCRGDCFC) into the S2 position. The three capsomers are represented with different colours, magenta, cyan and orange, with the inserted sequence shown in red, blue and yellow, respectively. According to the model, the RGD-4C ligand remains well exposed to the outer surface.

FIG. 7: Genetic insertion of the RGD-4C peptide into the viral capsid of the H-1PV-H373R mutant rescued viral infectivity (A) Electron microscopy analysis showing proper capsid assembly of the H-1PV-H373R-RGD-4C mutant.

(B) Virus production. After transfection of the viral DNA in HEK293 cells, virions were formed in similar amounts indicating that the insertion at this position did not impair virus assembly nor packaging.

(C) FACS analysis showing the protein levels of $\alpha_v\beta_3$ and $\alpha_v\beta_5$ integrins on the surface of NB324K.

(D) Infectivity. NB324K cells were infected with purified wild-type or RGD-4C-containing (RGD-4C) H-1PV viruses. Cells were collected 7 days post-infection (pi), and processed for viral DNA hybridization assay in order to assess the capacity of the viral particles (expressed as encapsidated Vg) to form infection units. Consistent with the lack of $\alpha_v\beta_3$ and $\alpha_v\beta_5$ integrins on the surface of NB324K cells, H-1RGD behaved similarly to the H373R de-targeted virus and did not efficiently infect these cells.

(E) Viral entry assay. SK-MEL-28 cells were cultured in 24-well plates, at a density of $10^5$ cells per well, and treated (+) or not (−) with 0.1 U/ml Neuraminidase (NA) for 3 h at 37° C. Cells were then infected with the indicated viruses used at the concentration of 500 Vg/ml, in triplicate for 6 h at 37° C. After washing to remove unbound virus, cells were harvested and lysed through three snap freeze/thaw cycles and viral DNA was purified and quantified as described in legend for FIG. 4. Columns represent percentage of input virions that were taken up. Numbers on top of columns give the ratios of cell-associated virions in untreated versus neuraminidase-treated cells. (F) The toxicity of the H-1PV mutants was evaluated on SK-MEL-2828 cells, which are permissive to H-1PV infection and overexpress $\alpha_v\beta_3$ and $\alpha v\beta 5$ integrins. Viable cells were determined via CellTiter-Glo® as described in Example 1 and represented as relative cell survival (%) considering as 100% survival, the luminescent value obtained in untreated cells (see also FIG. 12).

Figure 8:
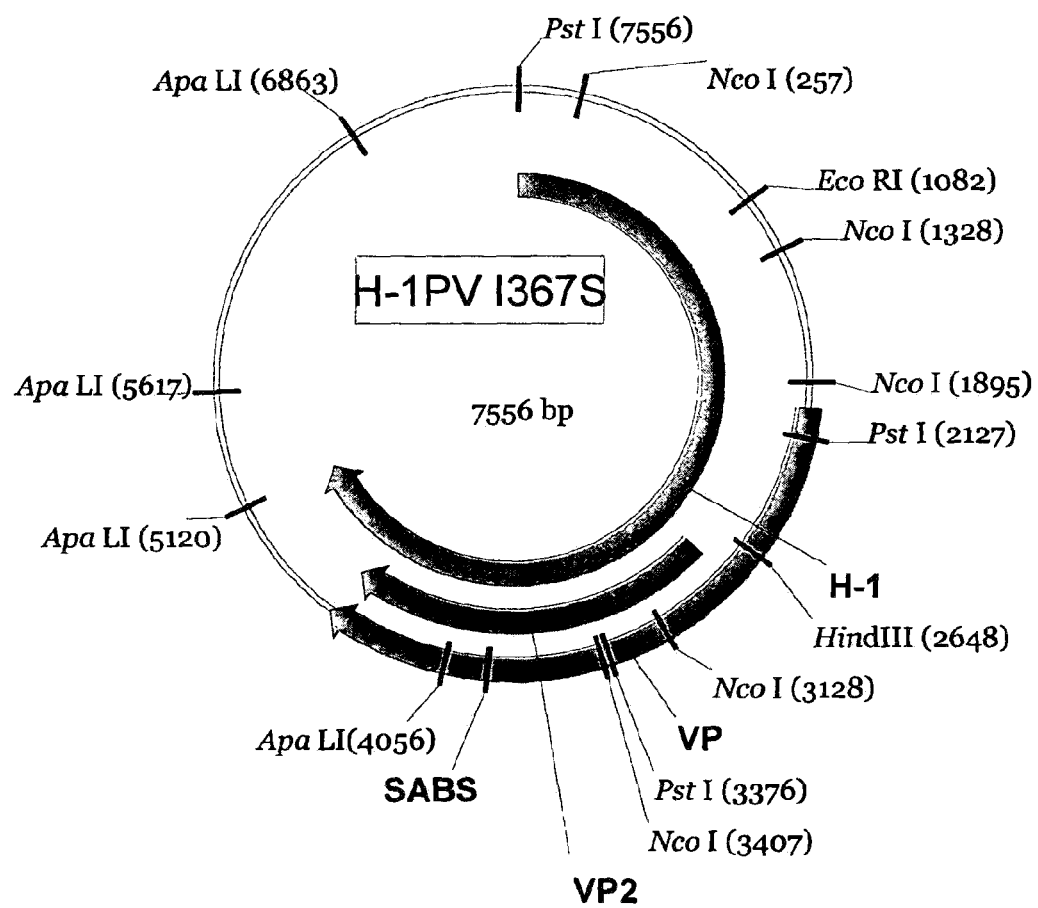

FIG. 8: Restriction map of clone H-1PV I367S

Figure 9:
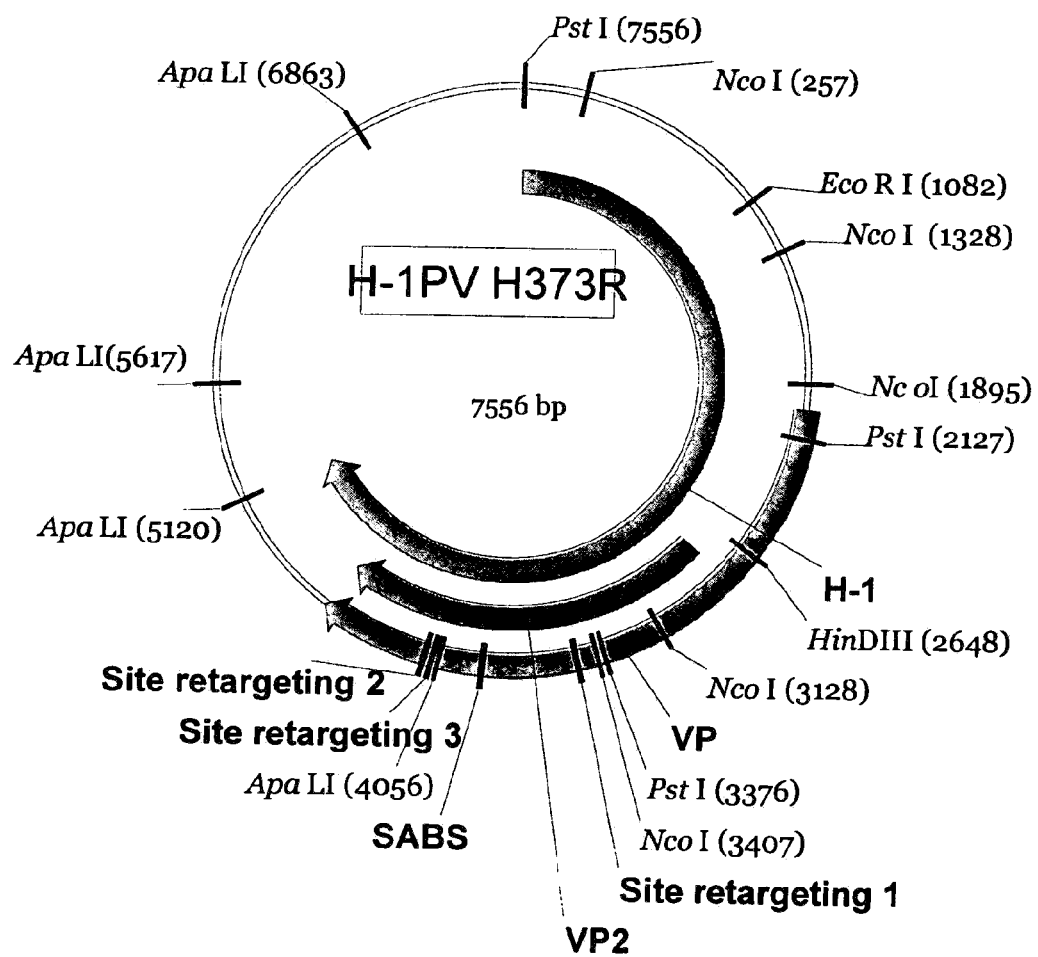

FIG. 9: Restriction map of clone H-1PV H373R

Figure 10:
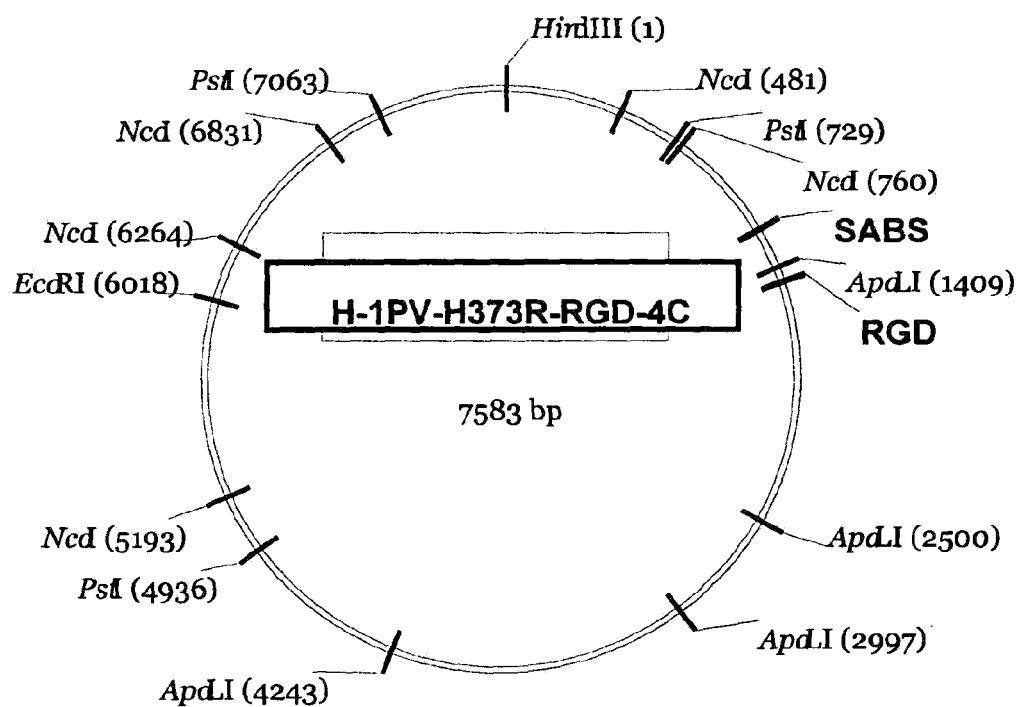

FIG. 10: Restriction map of clone RGD-4C-H-1PV H373R

Figure 11:
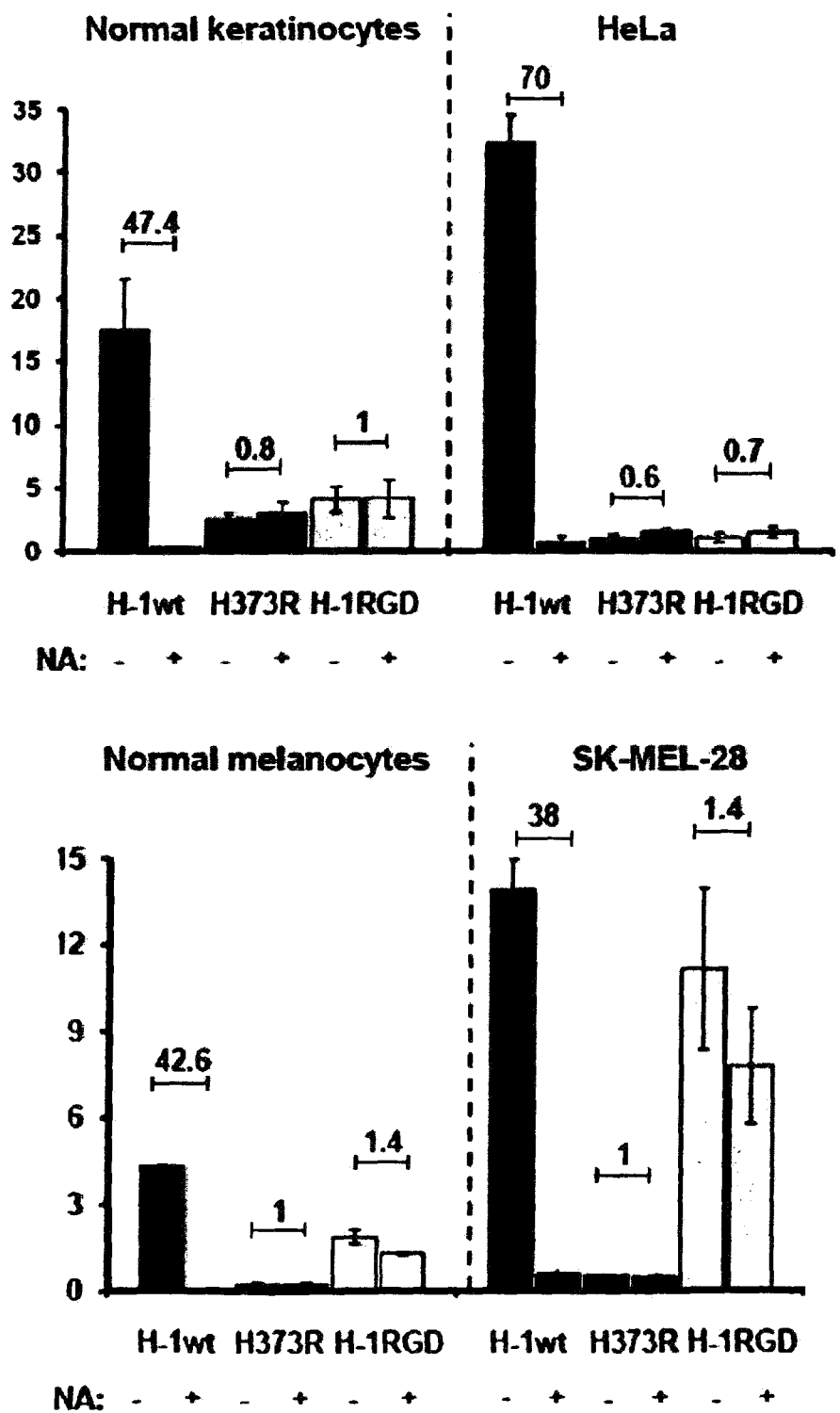

FIG. 11: Preferential H-1RGD infection of SK-MEL-28 cells displaying αvβ5 integrins on their surface (A) Integrin content. Cervical carcinoma-derived HeLa cells, SK-MEL-28 melanoma cells and their normal counterparts (primary normal keratinocytes and melanocytes) were grown for 48 h and analyzed by FACS for their surface expression of $\alpha_v\beta_3$ and $\alpha_v\beta_5$ integrins as described in Example 1.

(B) The above mentioned cells were treated (+) or not (−) with 0.1 U/ml neuraminidase (NA) for 3 h at 37° C., infected with the indicated viruses at the MOI of 500 Vg/cell and processed for the measurement of cell-associated virions (including both cell surface-bound and internalized viruses) as described in legend to FIG. 2. Columns represent percentage of input virions that were taken up. Numbers on top of columns give the ratios of cell-associated virions in untreated versus neuraminidase-treated cells.

Figure 12:
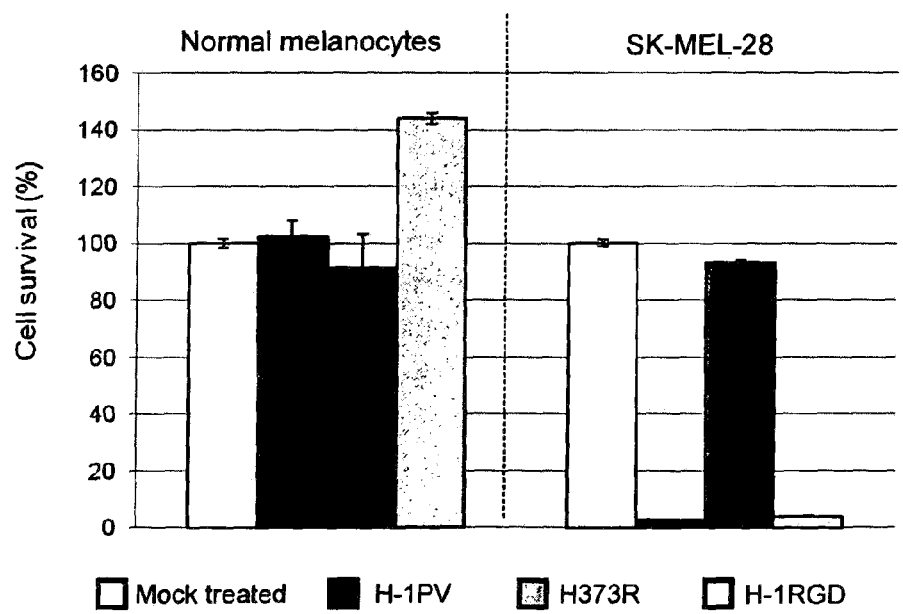

FIG. 12: Re-targeting H-1PV

Cell survival. The toxicity of the H-1PV mutants and parental viruses was evaluated in melanoma SK-MEL-28 cells and normal primary melanocytes. The survival of infected cells was determined as described in Example 1 and expressed as percentage relative to mock-treated cultures. Columns show means of triplicate measurements with standard deviation bars from one typical experiment formed in triplicates.

The insertion of the RGD-4C peptide does not impair the capacity of the virus to kill cancer cells; see Example 6 for further explanation.

The present invention provides an H-1 rat parvovirus (H-1PV) comprising a mutation in the polypeptide sequence of the VP proteins, wherein the mutation is at position I367 and/or H373 and/or A441 (VP2 protein) of H-1PV. The person skilled in the art can generate such a modified parvovirus using methods well known in the art using the published nucleotide sequence of H-1PV as starting material (61,62; see also the experimental procedure described in Example 1(C)).

The term "H-1PV" also relates to viruses that might comprise additional mutations besides the mutations of the present invention which do substantially effect its therapeutic usefulness as well as vectors based on such viruses. Suitable further modified parvoviruses, vectors as well as cells which can be used for actively producing said parvoviruses and which are useful for therapy, are readily determinable within the skill of the art based on the disclosure herein, without undue empirical effort.

In a preferred embodiment of the present invention, the mutation of H-1PV is an I367S mutation and/or an H373R mutation.

In a further preferred embodiment, the H-1 rat parvovirus of the invention further comprises a foreign protein with high-affinity for a receptor expressed in a tumor cell which is inserted at position A441. Examples of such foreign peptides are the RGD family members including the RGD-4C peptide, the peptidic ligands of known human specific receptors, such as the epidermal growth factor receptor that has been successfully used to retarget adenovirus to gliomas (55), peptide aptamers, peptide libraries, or other peptides selected through phage dispay screening approaches.

In a particularly preferred embodiment of the H-1PV of the present invention, the foreign protein comprises the amino acid sequence RGD (63). The person skilled in the art can select suitable sites within the capsid VP1 and VP2 proteins, for insertion of the foreign proteins applying, e.g., the approach described in Examples 2 and 5, below. The identification of places where to graft peptides opens the possibility to insert other retargeting peptides. An example (which does not exclude the use of other peptides) would be to insert a peptide targeting Delta-EGFR (epithelial growth factor receptor) which is also frequently over-expressed in gliomas (70) or, for example, a cervical carcinoma specific peptide described to retarget adenovirus to cervical carcinoma cells (71).

In an even more preferred embodiment of the H-1PV of the present invention, the foreign protein is inserted at position A441 of the VP2 protein of the parvovirus corresponding to A583 of the VP1 protein.

The present invention also provides a pharmaceutical composition containing the H-1PV of the invention.

Preferably, in said pharmaceutical composition the parvovirus is present in an effective dose and combined with a pharmaceutically acceptable carrier. "Pharmaceutically acceptable" is meant to encompass any carrier, which does not interfere with the effectiveness of the biological activity of the virus and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art (72).

Preferred doses for the parvovirus of the present invention are in the range of about $10^8$ to $10^9$ pfu (single injection).

Additional pharmaceutically compatible carriers can include gels, bioasorbable matrix materials, implantation elements containing the therapeutic agent, or any other suitable vehicle, delivery or dispensing means or material(s).

Administration of the H-1PV of the present invention may be effected by different ways, e.g. by intravenous, intraperetoneal, subcutaneous, intramuscular, topical or intradermal administration. The route of administration, of course, depends on the kind of therapy and the kind of further compounds contained in the pharmaceutical composition. A preferred route of administration is intravenous administration. The dosage regimen of the parvovirus is readily determinable within the skill of the art, by the attending physician based an patient data, observations and other clinical factors, including for example the patient's size, body surface area, age, sex, the time and route of administration, the tumor type and characteristics, general health of the patient, and other drug therapies to which the patient is being subjected.

If the parvovirus of the invention comprises infectious virus particles with, the ability to penetrate through the blood-brain barrier, treatment can be performed or at least initiated by intravenous injection of the parvovirus. A preferred route of administration is intratumoral administration.

Since long-term intravenous treatment is susceptible to becoming inefficient as a result of the formation of neutralizing antibodies to the parvovirus, different modes of administration can be adopted after an initial regimen intravenous viral administration, or such different administration techniques, e.g., intracranial or intratumoral virus administration, can be alternatively used throughout the entire course of parvoviral treatment.

As another specific administration technique, the H1-PV containing composition can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus containing composition to be injected locally at various times without further surgical intervention. The parvovirus or derived vectors containing composition can also be injected into the tumor by stereotactic surgical techniques or by neuronavi-gation targeting techniques.

Administration of the H-1PV of the invention containing compositions can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvovirus of the invention containing composition is from an implanted article constructed and arranged to dispense the parvovirus containing composition to the desired cancer tissue. For example, wafers can be employed that have been impregnated with the parvovirus containing composition wherein the wafer is attached to the edges of the resection cavity at the conclusion of surgical tumor removal. Multiple wafers can be employed in such therapeutic intervention.

The therapy based on the application of the pharmaceutical composition of the invention is useful for the therapeutic treatment of cancer, in particular a melanoma, a brain tumor, mammary carcinoma or cervix carcinoma. However, the therapy according to the present invention is, in principle, applicable to any tumor that can be infected with a parvovirus. The parvovirus H1 of the invention effects killing of tumor cells but does not harm normal cells and such infection can, for example, be carried out by intracerebral use of the virus or vector based on such virus, to effect tumor-specific therapy without adverse neurological or other side effects.

Patients treatable by the H-1PV according to the invention include humans as well as non-human animals. Examples of the latter include, without limitation, animals such as cows, sheep, pigs, horses, dogs, and cats.

The invention is further described by the following examples.

Example 1

Materials and Methods (A) VP2 Homology Modelling

Homology modelling of H-1 VP2 capsomer was performed at the CPHmodels 3.0 server of the Center for Biological Sequence Analysis from the Technical University of Denmark (www.cbs.dtu.dk/services/CPHmodels/), using as a template the already 3.25.ANG. resolved MVMpb VP2 1 Z14 3D crystal structure model (41), which shares 66.4% homology with H-1 VP2 capsomer within the 38-593 subsequence. The model obtained was then verified for stereochemical quality and further refined using PROCHECK (56), WHAT-CHECK (57), ERRAT (58), VERIFY-3D (59) and PROVE (60), all indicating that the overall capsomer was modeled with particularly high confidence.

(B) H-1 Capsid 3D Model

In order to produce a 3D model of H-1PV capsid, 60 copies of the VP2 model were assembled in PyMol (61) and aligned on the MVMpb 1Z14 model focusing on the Cα of the backbone. Alignment was achieved using the routine tool that first performs sequence alignment followed by structural alignment and then carries out cycles of refinement in order to reject structural outliers found during the fit. In order to obtain a "topographic" representation of the capsid surface, a homemade application was developed (Supplementary information). This application calculates the location of the center of mass of the virion from the capsid PDB file and then computes the distance between the center of mass and each of the atoms forming the capsid. Each "centre of mass-atom" distance is loaded into the original PDB file, replacing the b-factor field, and is finally displayed as a colored gradient using the PyMol program.

(C) Generation of H-1PV Mutants

For the construction of H-1PV mutants, a fragment of the viral genome containing the VP gene unit, obtained by digesting the pSR19 clone (62) with HindIII-HpaI, was first subcloned into pBSK-HpaI vector generating the pVPsub construct. pBSK-HpaI is a pBluescript SK+ plasmid (Stratagene) with a modified polylinker constructed by replacing the HindIII-XhoI fragment with an adapter containing a HpaI restriction site obtained by annealing the 5'-AGC TTA TCG ATA CCG TCG ACG TTA ACC-3', and 5'-TCG AGG TTA ACG TCG ACG GTA TCG ATA-3' oligonucleotides. In situ mutagenesis was performed using pVPsub as template as previously described (63), using the following primers (in bold the mutations introduced): for clone pVPsub I367S, 5'-GGT ACC GCT AGA CAG CAC AGC TGG CGA GG-3', and 5'-CCT CGC CAG CTG TGC TGT CTA GCG GTA CC-3'; for clone pVPsub H373R, 5'-GCT GGC GAG GAC CGT GAT GCA AAC GGA GC-3', and 5'-GCT CCG TTT GCA TCA CGG TCC TCG CCA GC-3'. The modified VP2s were finally cloned back in their parental pSR19 backbone in order to generate pH-1PV-I367S and pH-1PV-H373R detargeted mutans, using HindIII and HpaI restriction enzymes. The H-1PV-H373R-RGD-4C retargeted mutant was constructed by inserting the RGD-4C(CDCRGDCFC) peptide (64) into into A441 of VP2 capsid protein (corresponding to A583 of the VP1 protein) of the pH-1PV H373R mutant. (according to Swiss-Prot: P03136.1 sequence). For this purpose, overlap extension PCR (65) was performed using the following primers: RGD 1: 5'-GCC GCG GAG ACT GTT TCT GCG GCA GAA CTA ACA TGC A-3', RGD 2: 5'-AAC AGT CTC CGC GGC. AGT CAC AAG CTA TGG CGT CTT CTC-3' (with indicated RGD-4C related sequences indicated in bold), External 1: 5'-CGA AGA TTG GGC CAA AC-3', and External 2: 5'-TTT GTC CCA AAT TTG TCC-3'. The resulting PCR fragment was then cloned into the pH-1PV H373R clone using the MfeI-DraIII restriction enzymes.

(D) Cells

HEK293T (transformed human embryonic kidney), NB324K (newborn human kidney) and SK-MEL-28 (skin melanoma) cell lines were obtained from ATCC (LGS Standards GmBH, Wesel, Germany). HeLa (cervical carcinoma) cells were a gift from Dr. Alonso (German Cancer Research Center, Heidelberg, Germany). Primary keratinocytes and primary human adult melanocyte lightly pigmented (HEMa-LP) were purchased from PromoCell (Heidelberg, Germany) and Invitrogen (now part of Applied Biosystems, Darmstadt, Germany) respectively. 293T, HeLa and SK-MEL-28 cells were grown in Dulbecco's Modified Eagle's Medium supplemented with 10% FBS (Gibco, Invitrogen, Darmstadt, Germany). NB324K cells were grown in Minimum Essential Medium supplemented with 5% FBS. Primary melanocytes, were grown in medium 254 supplemented with HMGS (Invitrogen). Primary keratinocytes were grown in EpiLife-based medium containing human keratinocyte supplements (HKGS) (CAScade Biologics, Portland, Oreg.). All media, except the ones of primary melanocytes and keratinocytes, contained 2 mM L-glutamin, 100 U/ml penicillin and 100 µg/ml streptomycin. Cells were kept at 37° C. in 5% $CO_2$ and 92% humidity.

(E) Cellular Virus Binding and Entry Assays $5 \times 10^4$ cells/well were seeded in a 24-well plate and grown in ml of complete medium. After 21 h, cells were grown for further 3 h at 37° C. with or without 0.1 U/ml neuraminidase (Sigma-Aldrich Chemie GmbH, Steinheim, Germany). The culture medium was then removed and replaced with 0.5 ml serum-free medium containing H-1PV wild-type or mutant viruses at the multiplicity of infection (MOI) of 500 Vg/cell. For the binding assay, infection was carried out in triplicates for 1 or 2 h at 4° C. allowing the virus to bind to cellular surface receptors but not to enter into the cells. For the uptake assay, infection was for 2 h (NB324K, normal keratinocytes and HeLa) or 6 h (normal melanocytes and SK-MEL-28) at 37° C. for the viral cell uptake assay allowing internalization of bound viral particles. Infected cells were washed with 500 µl of PBS, harvested by treatment with trypsin (Gibco, Invitrogen, Darmstadt Germany) and resuspended in 200 µl of complete medium, which proved not to be accompanied by any detectable virus detachment from the cell surface (data not shown). Cells were then subjected to three snap freeze/thaw cycles to release the viral particles. Viral DNA was purified from the original virus inoculum and cell lysates using the QiaAmp MinElute Virus kit (Qiagen, Hilden, Germany) according to the manufacturer's instructions, and was quantified using the parvovirus specific qPCR described above.

For the results described in FIG. 5B, some modifications were introduced. In particular, cells were seeded in 48-well plate in 200 µl of complete medium. After 24 h, medium was removed and replaced by 200 µl of serum free medium containing purified viral preparation at the concentration of MOI of $10^4$ Vg/cell. After 30 min at 4° C., plates were washed with serum free medium in order to remove unattached particles, and then incubated for additional 2 h at 37° C. After washing with 500 µl of PBS, cells were then treated with 100 µl of trypsin 0.05% and the reaction stopped with 100 µl of complete medium.

(F) Cell Transfection and Virus Production $6 \times 10^6$ HEK293T cells were plated in 175 cm² flaskes and transiently transfected with 15 µg of viral plasmid/flask according to Reed et al. (66). After three days cells were harvested and viral particles released from cell suspension through three freeze-thaw cycles. Crude cell extracts were digested with Benzonase Nuclease (Ultrapure grade) (Sigma) 50 U/ml, 37° C. for 30 min. Viruses were purified using a Iodixanol discontinuous gradient according to Zolotukhin et al. (67). Produced viral particles were quantified by qPCR (see below) and represented as encapsidated viral genomes (Vg). Further amplification of the viral stocks was conducted via infection of the NB324K cell line using at the MOI of 100 Vg/cell. Cells were harvested after 5-7 days post-infection and treated as described above.

(G) Virus Titration

Quantitative real time polymerase chain reaction (qPCR) and plaque assays were performed as previously described (68). Infection unit (IU) assays were carried out in 96-well plates seeded with $7.5 \times 10^3$ cells/well (NB324K or HEK293T) or $5 \times 10^3$ (HeLa) cells/well. One day after seeding, cells were infected with 10-fold serial dilutions of the virus stocks and incubated for 72 h at 37° C., 5% $CO_2$. After alkaline lysis (0.75 M NaOH) of infected cells, DNA was transferred to a nylon membrane, cross linked and hybridized to a $^{32}$P-radiolabbeled NS-1-specific probe corresponding to the EcoRV (nt 385)-EcoRI (nt 1084) fragment of pMVM plasmid. Blots were exposed to X-ray film for autoradiography. Titration experiments were always performed at least in duplicates.

(H) Quantitative Real Time Polymerase Chain Reaction (qPCR)

Crude cell extracts were digested with Benzonase® Nuclease (Ultrapure grade [Sigma-Aldrich Chemie GmbH, Steinheim, Germany], 50 U/ml, 37° C. for 30 min) to eliminate genomic DNA and remaining transfected plasmids. To release viral DNA from virions, 10 µl of cell extract were mixed with 30 µl of alkaline lysis buffer (1 M NaOH in TE buffer) at 56° C. for 30 min. Lysis was stopped by adding 960 µl of 40 mM HCl.

Quantification of viral DNA was carried out by real-time qPCR with the NS1-specific TaqManm probe, 5'-6-FAM ATG CAG CCA GAC AGT TA-MGB-3' (Applied Biosystems, Darmstadt, Germany), using the following primers NS1-FOR: 5'-GCG CGG CAG AAT TCA AAC T-3' and NS1-REV 5'-CCA CCT GGT TGA GCC ATC AT-3'. PCRs were carried out using a ABI Prism 7700 thermal cycler (Applied Biosystems, Darmstadt, Germany), and analyzed by means of SDS 2.1 software (Applied Biosystems). A plasmid containing the NS1 sequence was serial diluted in the range of $10^1$-$10^8$ copies/reaction and was used to standardize the qPCR. Individual reaction mixtures (20 µl) consisted of 1× TaqMan Universal PCR Master Mix™ (Applied Biosystems), 0.3 µM labeled NS1-TaqManm probe, 0.3 µM of each primer and 3 µl of template.

(I) Electron Microscopy

Carbon-coated 300-mesh copper grids were placed face down onto 5 µl aliquots of virus suspension for 2 min, stained with 2% uranylacetate for 30 s, and dried for approx. 1 min. Micrographs were taken at a magnification of 20,100-fold with a Zeiss 10A electron microscope (Zeiss, Oberkochen, Germany) using an acceleration voltage of 80 kV. The magnification indicator was routinely controlled by comparison with a grating replica.

(J) Cell Viability Assay

Virus toxicity for primary melanocytes and SK-MEL-28 cells was determined using the CellTiter-Glo® assay (Promega, Mannheim, Germany), which measures the culture's ATP content as an indicator of metabolically active viable cells. Briefly, cells were seeded in an opaque-walled 96-well plate at a density of 2000 cells/well in 50 µl of medium. After incubation for 24 h, cells were infected with purified virus (200,000 Vg for primary melanocytes, 500,000 Vg for SK-MEL-28) diluted in 50 µl of medium. At day 5 after infection, 80 µl of CellTiter-Glo® reagent was directly added to the cell medium. After orbital shaking for 2 minutes, cultures were further incubated at room temperature for 10 min. The cellular glowing signal was then measured using the plate-reading luminometer Fluoroskan (Ascent FL, Thermo Labsystems, Dreieich, Germany). Wells containing only medium were used for background evaluation. Percentages of cell viability were calculated from the ratios of the luminescent values of virus-infected versus mock-treated cultures after background subtraction.

(K) Plaque Assay

NBK cells grown in monolayer were infected with serial dilutions of crude virus suspension for 1 h, followed by replacement of the inoculum with an overlay of 0.68% Bacto™ Agar (Becton, Dickinson and Company) in Mimimum Essential Medium[+]L-Glutamine (Gibco, Invitrogen, Darmstadt Germany) containing 5% FBS, 2 mM L-Glutamine, 100 U/ml Penicillin, 100 µg/ml Streptomycin. 5 days post infection, living cells were stained for 18 h by addition of neutral-red (0.2 mg/ml)—containing Bacto™ Agar (0.85%) diluted in PBS. Plaques were counted and titers were expressed as plaque-forming units (PFU) per ml (L) Infection Unit Assays NBK or 293T/17 indicator cells were seeded in 6 cm dishes at a density of $5\times10^5$ cells per dish. After 24 h, crude virus suspensions, serially diluted (in 1:10 steps), were used to infect the indicator cells in a total volume of 400 µl. After 1 h incubation at 37° C. and plates shaking every 10 min, 5 ml of medium was added to every dish. At 72 h post infection, cell layers were washed with PBS, and nitrocellulose filters of 25 mm diameter (Schleicher & Schuell, Dassel, Germany) were applied on top of the cells and moisturized with 100 µl of PBS. The filters were subsequently put upside down on Whatman paper saturated with denaturation buffer (0.5 M NaOH and 1.5 M NaCl) for 5 min. Filters were then transferred to Whatman paper saturated with neutralizing buffer (0.5 M Tris/HCl [pH 7.2], 1.5 M NaCl and 1 mM EDTA) for additional 5 min. DNA was fixed by baking the filters at 80° C. for 2 h. Prehybridization was performed in 3×SSC (1×SSC is 0.15 M NaCl plus 0.015 M sodium citrate), 1% SDS, 5 mM EDTA, 10×Denhardt's solution and 100 µg/ml salmon sperm DNA, at 65° C. for 1 h. Hybridization was carried out by addition of the radioactive probe corresponding to the EcoRV (nt 385)-EcoRI (nt 1084) fragment of pMVM plasmid, purified by agarose gel electrophoresis, and labeled with [$^{32}$P]dCTP using the Megaprime DNA Labeling System (GE Healthcare). After incubation at 65° C. over night, filters were washed first in 3×SSC (pH 7), 1% SDS at 65° C. for 30 min, then in 0.3×SSC (pH 7) at 65° C. for 30 min. Subsequently, filters were placed on Whatman paper, wrapped in plastic foil and exposed to a radiographic film at −80° C. overnight. Cells supporting viral DNA amplification appear as black dots on the film due to the hybridization with radioactively labeled viral DNA. Virus titers were calculated as number of black dots×dilution factor×7.5, and expressed in infectious units (IU) per ml.

(M) Determination of Integrin Expression by Flow Cytometry

Cells were harvested and centrifuged at 1500 rpm for 5 min at room temperature. Pellets were resuspended in fresh medium, cooled on ice and then washed in FACS buffer (PBS supplemented with 10% FCS and 0.01% NaN$_3$) at 4° C. $2\times10^5$ cells were incubated in a total volume of 100 µl for 90 min on ice with either of the following antibodies (all Millipore, Temecula, Calif.): (i) 1:50 dilution of mouse IgG$_1$-FITC isotype control, clone Ci4; (ii) 4 µg/ml mouse $\alpha_v\beta_3$-FITC, clone LM609; and (iii) 4 µg/ml mouse $\alpha_v\beta_5$-FITC, clone P1F6. Cells were washed twice with 1 ml FACS buffer and finally resuspended in 700 µl FACS buffer. Cells were analyzed by flow cytometry (FACSort, Becton Dickinson, Franklin Lakes, NJ) and data was evaluated using FCS Express Version 3 (De Novo Software, Los Angeles, Calif.).

Example 2

In Silico Modeling of H-1PV Capsid

Figure 1:
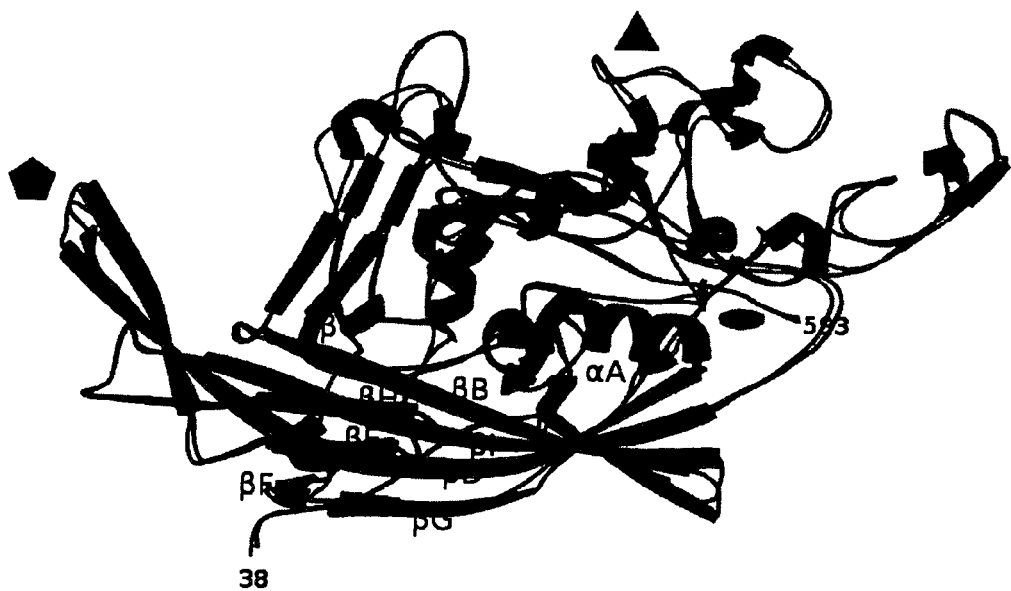
FIG. 1: In silico model of H-1PV VP2 capsid protein

As the crystal structure of H-1PV capsid has been not yet been resolved, we constructed an in silico 3D model of the H-1 capsid by homology with the resolved crystal structure of the closely related MVM parvovirus. We first modelled the structure of the H-1PV VP2 capsid protein. As shown in FIG. 1, the topology of the modelled H-1PV VP2 is similar to other parvovirus capsid proteins. An eight-stranded β-barrel motif (βB to βI) forms the core contiguous capsid, decorated by loop insertions between the β-strands. Other smaller β secondary structures can also be found inside the loops, like in CPV or MVM, but in different places. According to our model, the H-1PV VP2 protein contains a small α-helix (αA) domain spanning residues 126 to 137 in the vicinity of the icosahedral twofold axis, a sequence that is conserved in all the parvovirus structures determined so far (69) (FIG. 1).

The VP2 protein represents more than 90% of the 60 H-1 VP units. In the case of MVM, it has been described that virus-like particles only made of VP2 were not significantly different from models obtained from full wild-type virions (43). Therefore, we decided to model the H-1PV capsid based on VP2 only. In order to form the complete H-1 capsid 3D model, 60 copies of the VP2 model were cloned in PyMol and aligned on the MVMpb crystal structure model (see Example 1 for a detailed description of the parameters adopted for the modelling). The resulting T=1 icosahedral capsid model displays all the main structural features of a characteristic mammalian autonomous parvovirus capsid such as: (i) a fivefold axis pore surrounded by a canyon formed by the clustering of five symmetry-related-ribbons; (ii) a threefold axis spike, resulting from the clustering of six large surface loops, two from each threefold-symmetry-related VP2 subunit and (iii) a twofold axis dimple (FIG. 2A). H-1 and MVM capsids are very similar in this respect, with comparable geometries. In both capsids, the 5-fold axis pore structure is approximately 130 Å distant from the hypothetical center of the capsid (FIG. 2B), while the 3-fold axis spike (FIG. 2C) and the 2-fold axis dimple (FIG. 2D) are respectively 145 and 100 Å far from the center, respectively. The center of the threefold axis spikes seems slightly less protruding in H-1 compared to MVM (~130 Å vs. ~135 Å), and it is surrounded by three off-cantered apexes due to the exposed side chain of GLU 233.

Example 3

Sialic Acid is Involved in H-1PV Cell Membrane Recognition and Entry

Analysis of the model suggests that the two-fold axis dimple, is conserved in MVM and H-1PV (FIG. 3). In MVM, this region binds to sialic acid, which appears to be important for cellular entry (10). In particular two residues of the MVM capsomers have been shown to bind to sialic acid at the surface of this region (40-42). Treatment with neuraminidase, which cleaves the sialic acid from surface proteins, was shown to greatly impair MVM cellular entry. Sialic acid is also involved in the binding of the H-1 capsid to the cell membrane: two highly H-1PV permissive cell lines, HeLa and NBK were grown in the presence or absence of neuro-minidase before H-1PV infection. Pretreatment with neuraminidase dramatically decreased (approximately 95%) the capacity of both HeLa and NB324K cells to take up the virus, indicating that, similar to MVM, H-1PV interacts with sialic acid and this binding is important for parvovirus infection (FIG. 4 and data not shown).

Example 4

H-1PV Detargeting by In Situ Mutagenesis

To redirect viral tropism at the level of receptor recognition, it is first important to ablate the binding of the virus to its natural receptor(s) (de-targeting). As sialic acid seems to mediate cell surface recognition of both MVM and H-1PV, we hypothesized that similarly to MVM, the dimple region of H-1PV may be also involved in the interaction with the sugar. In MVM, both I362 and K368 are involved in the binding to sialic acid. Based on mass and charge properties and in silico modeling, we decided to singly substitute I367 and H373 with S and R, respectively, thus generating the H-1PV I367S and H1PV H373R mutants. After viral DNA transfection in HEK293T cells, viral particles with apparent normal morphology were formed (FIG. 5A).

The mutations did however strongly affect viral binding and entry in both NBK and HeLa cells (FIG. 5B) with more than 90% reduction observed for the virus carrying the modification at the residue 373. Infection unit and plaque assays confirmed a reduction in the number of infectious particles that entered the cells as a result of the mutations introduced (FIG. 5C).

Furthermore, although mutant viruses were produced at lower titres in comparison to wild-type H-1PV (FIG. 5D), no differences in terms of stability were observed between the different viral batches (data not shown). In addition, similarly to NB324K cells, the mutations did strongly affect viral binding and entry into HeLa cells (FIG. 5E) with more than 90% reduction observed for the virus carrying the modification at residue 373. Viral DNA hybridization assays performed in NB324K, HeLa and HEK293T cells confirmed that as a result of the introduced substitutions the number of mutant particles being able to enter the cells in order to initiate their replication cycle was strongly reduced (FIG. 5F). In agreement with previous results, inhibition was much more evident for the H373R than for the I367S mutant. Consistently, both mutations also impaired the capacity of the virus to form plaques in NB324K with a strong effect observed for the H373R substitution (FIG. 5G). The two mutant viruses also displayed a reduced ability to lyse cells and halt their proliferation, as measured by LDH and MTT assays respectively (data not shown).

Example 5

Retargeting of Entry Defective H-1PV H373R Mutant to Alpha5Beta5 Integrins by Insertion of a Cyclic RGD Peptide into its Capsid The results presented above indicated that the H373R substitution within the VP proteins dramatically reduced both virus cell membrane recognition and entry while maintaining the capacity of the proteins to properly assemble and form the capsid. The second step of the genetic reprogramming of H-1PV, was to further modify this entry-defective mutant by inserting cancer-specific retargeting peptides into its capsid that could confer the virus a distinct oncotropism at the level of viral-entry.

αvβ3 and αvβ5 integrins are often over-expressed in cancer cells. These integrins are efficiently recognized by peptides containing a RGD motif. In particular, a cyclic RGD-containing peptide (amino acid sequence: CDCRGDCFC) known as RGD-4C, composed of a central RGD motif surrounded by four cystein residues (that structurally stabilize the peptide by forming two disulfite bounds) is one of the most potent in recognizing αvβ3 and αvβ5 integrins (48, 49) and has been successfully used for the retargeting of Adenoviruses and AAVs (52-54). We started by identifying a position within the viral capsid that would ensure exposure of the peptide at the outer surface of the capsid while preserving its retargeting characteristics. We relied on our in silico capsid model to screen for potential insertion sites, paying special attention to two aspects of the capsid surface: (i) the level of protrusion; and (ii) the hydrophilic nature increasing the chances of the peptide being exposed to the outside. There were two VP residues (depicted as S1 and S2 sites in FIG. 6) that met these criteria in particular. They correspond to Gly 234 and Ala 441 in the VP2 sequence and are located in two loops present at the spikes of the threefold axis of symmetry (FIGS. 6A and B). We predicted that the RGD-4C peptide inserted in these positions would be well exposed at the outer surface (FIG. 6C) and inserted the RGD-4C next to a nitro carboxy group of Ala 441 of VP2 protein sequence (S2 site) to generate the H-1PV H373R-RGD-4C mutant (abbreviated to H-1RGD).

Figure 7A:
Figure 7B:
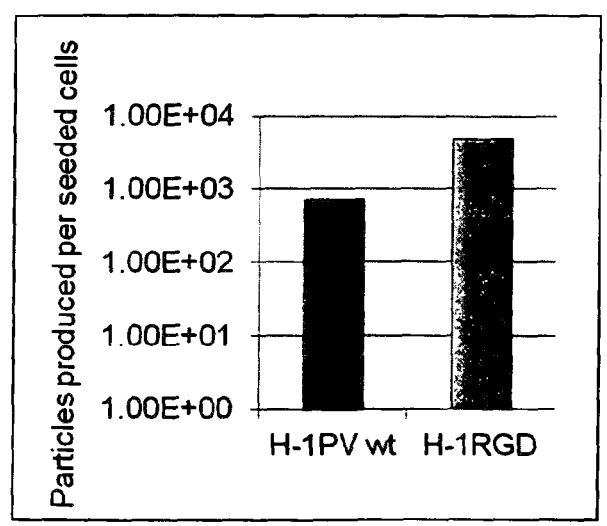

After transfection of the viral DNA in HEK293 cells, virions were formed in similar amounts and had the same morphological appearance of wild-type virions indicating that the insertion at this position did not impair virus assembly nor packaging (FIGS. 7A and B). We then tested the capacity of H-1RGD to infect NB324K in comparison to the wild-type virus. Expression of $\alpha_v\beta_3$ and $\alpha_v\beta_5$ integrins was under our detection limit in these cells (FIG. 7C). Consistent with the lack of $\alpha_v\beta_3$ and $\alpha_v\beta_5$ integrins on the surface of NB324K cells, H-1RGD behaved similarly to the H373R de-targeted virus and did not efficiently infect these cells (FIG. 7D).

Figure 7E:
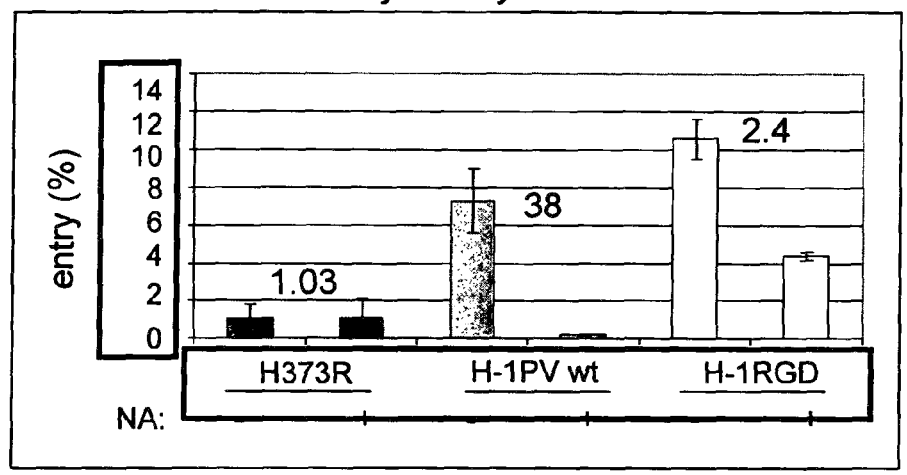
Figure 7F:
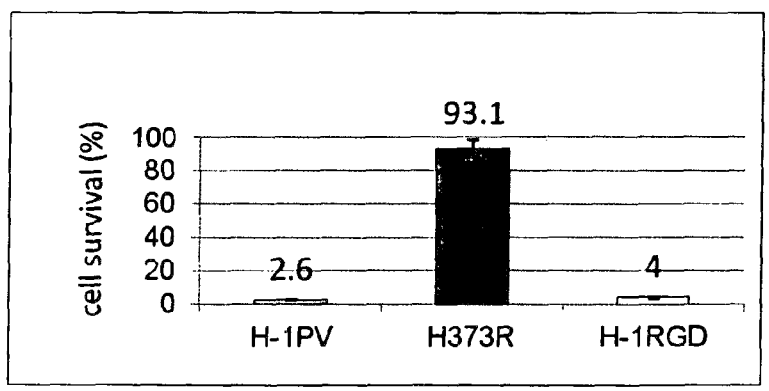

Then, cell entry assays were performed using SK-MEL-28 skin melanoma cells which are known to over-express $\alpha_v\beta_3$ and $\alpha_v\beta_5$ integrins (70, 71). As shown in FIG. 7E, the wild type virus was able to enter these cells, but viral entry was almost completely abolished by pre-treating the cells with neuraminidase, suggesting that, as in HeLa and NBK cells, the virus needs surface cellular sialic acid to enter SK-MEL-28 cells. As expected, the entry defective H-1PV H373R mutant was unable to infect SK-MEL-28 cells. Remarkably, the insertion of the RGD-4C peptide into this mutant, rescued its entry into the cells to a great extent. Importantly, viral entry was only partially sensitive to neuraminidase treatment, indicating that the RGD-4C containing virus infects the cells through an alternative pathway, independent of sialic acid (FIG. 7E). It was also investigated whether the anti-neoplastic features of the virus were affected by capsid modification by assessing the efficacy of the RGD-4C containing virus to kill SK-MEL-28 cells. Cell viability assays showed that the inability of H-1PV H373R to infect cells correlated very well with its failure to kill them. On the contrary, RGD-4C containing virus effectively killed SK-MEL-28 cells (FIG. 7F). Altogether these experiments demonstrate that the H-1PV viral capsid can be modified according to the invention to increase its affinity for cancer cells at the level of viral entry.

Example 6

H-1RGD Specificity for Melanoma Cells Expressing $\alpha_v\beta_5$ Integrins

In this example similar results as in example 5 are shown with additional controls.

It was tested whether the RGD-4C insertion led to virus retargeting onto human cancer cells versus normal human primary cells. Internalization assays were performed using SK-MEL-28 skin melanoma cells which over-express $\alpha_v\beta_3$ and $\alpha_v\beta_5$ integrins (70, 71). For comparison, HeLa cells were also tested together with primary cultures of non-transformed human melanocytes and keratinocytes. Flow cytometric analysis confirmed the high expression of $\alpha_v\beta_3$ and $\alpha_v\beta_5$ integrins in SK-MEL-28. It was also found that primary melanocytes expressed preferentially $\alpha_v\beta_3$ integrins while almost no expression of both $\alpha_v\beta_3$ and $\alpha_v\beta_5$ integrins was detected in primary keratynocytes and HeLa cells (FIG. 11A). As shown in FIG. 11B, the wild-type virus was taken up by all these different cultures in a sialic acid-dependent way, as viral entry was dramatically reduced by pre-treating cultures with neuraminidase. These results further confirmed the previous data obtained in HeLa and NB324K cells, showing that wild-type virus uptake is dependent on surface sialic acid. As expected, the H373R detargeted virus was unable to bind to the membrane and enter HeLa cells. Similar inefficiency was also found in SK-MEL-28 and normal cell cultures. Remarkably, the insertion of the RGD-4C peptide into the detargeted virus, rescued its entry into the $\alpha_v\beta_3^+/\alpha_v\beta_5^+$ melanoma cells to a great extent. Binding and entry of H-1RGD was only partially sensitive to neuraminidase treatment indicating that the H-1RGD virus infected the cells through an alternative route independent of sialic acid. The RGD peptide displayed on H-1RGD virus also correlated with some rescue of $\alpha_v\beta_3^+$ normal melanocytes but at a much lower level compared with melanoma cells. In contrast, RGD insertion dependent rescue was not significant in integrins-negative HeLa cells and normal keratinocytes. Altogether, these data show that the presence of $\alpha_v\beta_3$ and $\alpha_v\beta_5$ integrins at the cell surface allows H-1RGD uptake with low and high efficiency respectively (FIGS. 11A and B).

Next, it was investigated whether the RGD-mediated retargeting of H-1RGD onto integrin-positive melanoma (SK-MEL-28) cells was reflected in an enhanced oncolytic capacity of this virus compared with the detargeted H373R mutant. As shown in FIG. 12 (left panel), normal melanocytes resisted infection with both modified viruses as well as wild-type H-1PV, in keeping with the tumour specificity of parvovirus cytotoxicity. In contrast, the H-1RGD and parental viruses could be distinguished from the H373R mutant by their capacity to effectively kill melanoma cells (FIG. 12, right panel). Thus, the RGD insertion into the H373R mutant rescued not only the entry (see above), but also the cytopathic effect of this virus in melanoma cells, suggesting that after internalization, H-1RGD was competent for the expression of viral toxic proteins. Indeed, production of NS1, known to be the main effector of parvovirus-induced cell disturbances, could be detected at high levels in melanoma cells infected with H-1RGD (and wild-type) virus, but not H373R mutant (data not shown). In conclusion, these experiments demonstrate that the H-1PV capsid can be genetically modified to direct this virus at the surface of distinct cancer cells, while preserving the viral oncolytic potential.

LIST OF REFERENCES

1. Siegl G. Biology and pathogenicity of autonomous parvoviruses. In: Berns K I, editor. The parvoviruses. New York, N.Y.: Plenum Press, Inc.; 1983. p. 297-362.
2. Mousset S, Rommelaere J. Minute virus of mice inhibits cell transformation by simian virus 40. Nature 1982; 300 (5892):537-9.
3. Cornelis J J, Becquart P, Duponchel N, Salome N, Avalosse B L, Namba M, et al. Transformation of human fibroblasts by ionizing radiation, a chemical carcinogen, or simian virus 40 correlates with an increase in susceptibility to the autonomous parvoviruses H-1 virus and minute virus of mice. J Virol 1988; 62(5):1679-86.
4. Telerman A, Tuynder M, Dupressoir T, Robaye B, Sigaux F, Shaulian E, et al. A model for tumor suppression using H-1 parvovirus. Proc Natl Acad Sci USA 1993; 90(18): 8702-6.
5. Rommelaere J, Geletneky K, Angelova A L, Daeffler L, Dinsart C, Kiprianova I, et al. Oncolytic parvoviruses as cancer therapeutics. Cytokine Growth Factor Rev 2010; 21(2-3):185-95.
6. Grekova S, Zawatzky R, Horlein R, Cziepluch C, Mincberg M, Davis C, et al. Activation of an antiviral response in normal but not transformed mouse cells: a new determinant of minute virus of mice oncotropism. J Virol 2010; 84(1): 516-31.
7. Cornelis J J, Deleu L, Kock U, Rommelaere J. Parvovirus oncosuppression. London: Arnold E Ltd; 2006.
8. Etingov I, Itah R, Mincberg M, Keren-Naus A, Nam H J, Agbandje-McKenna M, et al. An extension of the Minute Virus of Mice tissue tropism. Virology 2008; 379(2):245-55.
9. Rubio M P, Lopez-Bueno A, Almendral J M. Virulent variants emerging in mice infected with the apathogenic prototype strain of the parvovirus minute virus of mice exhibit a capsid with low avidity for a primary receptor. J Virol 2005; 79(17):11280-90.
10. Lopez-Bueno A, Rubio M P, Bryant N, McKenna R, Agbandje-McKenna M, Almendral J M. Host-selected amino acid changes at the sialic acid binding pocket of the parvovirus capsid modulate cell binding affinity and determine virulence. J Virol 2006; 80(3):1563-73.
11. Kruger L, Eskerski H, Dinsart C, Cornelis J, Rommelaere J, Haberkorn U, et al. Augmented transgene expression in transformed cells using a parvoviral hybrid vector. Cancer Gene Ther 2008; 15(4):252-67.
12. Muller O J, Kaul F, Weitzman M D, Pasqualini R, Arap W, Kleinschmidt J A, et al. Random peptide libraries displayed on adeno-associated virus to select for targeted gene therapy vectors. Nat Biotechnol 2003; 21(9):1040-6.
13. Girod A, Ried M, Wobus C, Lahm H, Leike K, Kleinschmidt J, et al. Genetic capsid modifications allow efficient re-targeting of adeno-associated virus type 2. Nat Med 1999; 5(9):1052-6.
14. Michelfelder S, Kohlschutter J, Skorupa A, Pfennings S, Muller O, Kleinschmidt J A, et al. Successful expansion but not complete restriction of tropism of adeno-associated virus by in vivo biopanning of random virus display Peptide libraries. PLoS One 2009; 4(4):e5122.
15. Waterkamp D A, Muller O J, Ying Y, Trepel M, Kleinschmidt J A. Isolation of targeted AAV2 vectors from novel virus display libraries. J Gene Med 2006; 8(11):1307-19.
16. Krasnykh V, Dmitriev I, Mikheeva G, Miller C R, Belousova N, Curiel D T. Characterization of an adenovirus vector containing a heterologous peptide epitope in the HI loop of the fiber knob. J Virol 1998; 72(3):1844-52.
17. Gonzalez R, Vereecque R, Wickham T J, Vanrumbeke M, Kovesdi I, Bauters F, et al. Increased gene transfer in acute myeloid leukemic cells by an adenovirus vector containing a modified fiber protein. Gene Ther 1999; 6(3):314-20.
18. Coughlan L, Vallath S, Saha A, Flak M, McNeish I A, Vassaux G, et al. In vivo retargeting of adenovirus type 5 to alphavbeta6 integrin results in reduced hepatotoxicity and improved tumor uptake following systemic delivery. J Virol 2009; 83(13):6416-28.
19. Herrero Y C M, Cornelis J J, Herold-Mende C, Rommelaere J, Schlehofer J R, Geletneky K. Parvovirus H-1 infection of human glioma cells leads to complete viral replication and efficient cell killing. Int J Cancer 2004; 109(1):76-84.
20. Malerba M, Daeffler L, Rommelaere J, Iggo R D. Replicating parvoviruses that target colon cancer cells. J Virol 2003; 77(12):6683-91.
21. Faisst S, Guittard D, Benner A, Cesbron J Y, Schlehofer J R, Rommelaere J, et al. Dose-dependent regression of HeLa cell-derived tumours in SCID mice after parvovirus H-1 infection. Int J Cancer 1998; 75(4):584-9.
22. Van Pachterbeke C, Tuynder M, Brandenburger A, Leclercq G, Borras M, Rommelaere J. Varying sensitivity of human mammary carcinoma cells to the toxic effect of parvovirus H-1. Eur J Cancer 1997; 33(10):1648-53.

23. Van Pachterbeke C, Tuynder M, Cosyn J P, Lespagnard L, Larsimont D, Rommelaere J. Parvovirus H-1 inhibits growth of short-term tumor-derived but not normal mammary tissue cultures. Int J Cancer 1993; 55(4):672-7.
24. Ran Z, Rayet B, Rommelaere J, Faisst S. Parvovirus H-1-induced cell death: influence of intracellular NAD consumption on the regulation of necrosis and apoptosis. Virus Res 1999; 65(2):161-74.
25. Ohshima T, Iwama M, Ueno Y, Sugiyama F, Nakajima T, Fukamizu A, et al. Induction of apoptosis in vitro and in vivo by H-1 parvovirus infection. J Gen Virol 1998; 79 (Pt 12):3067-71.
26. Rayet B, Lopez-Guerrero J A, Rommelaere J, Dinsart C. Induction of programmed cell death by parvovirus H-1 in U937 cells: connection with the tumor necrosis factor alpha signalling pathway. J Virol 1998; 72(11):8893-903.
27. Ueno Y, Harada T, Iseki H, Ohshima T, Sugiyama F, Yagami K. Propagation of rat parvovirus in thymic lymphoma cell line C58(NT)d and subsequent appearance of a resistant cell clone after lytic infection. J Virol 2001; 75(8):3965-70.
28. Hristov G, Kramer M, Li J, El-Andaloussi N, Mora R, Daeffler L, et al. Through Its Nonstructural Protein NS1, Parvovirus H-1 Induces Apoptosis via Accumulation of Reactive Oxygen Species. J Virol 2010; 84(12):5909-22.
29. Di Piazza M, Mader C, Geletneky K, Herrero Y C M, Weber E, Schlehofer J, et al. Cytosolic activation of cathepsins mediates parvovirus H-1-induced killing of cisplatin and TRAIL-resistant glioma cells. J Virol 2007; 81(8):4186-98.
30. Cotmore S F, Tattersall P. Parvoviral host range and cell entry mechanisms. Adv Virus Res 2007; 70:183-232.
31. Parker J S, Murphy W J, Wang D, O'Brien S J, Parrish C R. Canine and feline parvoviruses can use human or feline transferrin receptors to bind, enter, and infect cells. J Virol 2001; 75(8):3896-902.
32. Summerford C, Samulski R J. Membrane-associated heparan sulfate proteoglycan is a receptor for adeno-associated virus type 2 virions. J Virol 1998; 72(2):1438-45.
33. Summerford C, Bartlett J S, Samulski R J. AlphaVbeta5 integrin: a co-receptor for adeno-associated virus type 2 infection. Nat Med 1999; 5(1):78-82.
34. Qing K, Mah C, Hansen J, Zhou S, Dwarki V, Srivastava A. Human fibroblast growth factor receptor 1 is a co-receptor for infection by adeno-associated virus 2. Nat Med 1999; 5(1):71-7.
35. Di Pasquale G, Davidson B L, Stein C S, Martins I, Scudiero D, Monks A, et al. Identification of PDGFR as a receptor for AAV-5 transduction. Nat Med 2003; 9(10):1306-12.
36. Brown K E, Anderson S M, Young N S. Erythrocyte P antigen: cellular receptor for B19 parvovirus. Science 1993; 262(5130):114-7.
37. Munakata Y, Saito-Ito T, Kumura-Ishii K, Huang J, Kodera T, Ishii T, et al. Ku80 autoantigen as a cellular coreceptor for human parvovirus B19 infection. Blood 2005; 106(10):3449-56.
38. Weigel-Kelley K A, Yoder M C, Srivastava A. Alpha5beta1 integrin as a cellular coreceptor for human parvovirus B19: requirement of functional activation of beta1 integrin for viral entry. Blood 2003; 102(12):3927-33.
39. Hueffer K, Parrish C R. Parvovirus host range, cell tropism and evolution. Curr Opin Microbiol 2003; 6(4):392-8.
40. Lopez-Bueno A, Segovia J C, Bueren J A, O'Sullivan M G, Wang F, Tattersall P, et al. Evolution to pathogenicity of the parvovirus minute virus of mice in immunodeficient mice involves genetic heterogeneity at the capsid domain that determines tropism. J Virol 2008; 82(3):1195-203.
41. Kontou M, Govindasamy L, Nam H J, Bryant N, Llamas-Saiz A L, Foces-Foces C, et al. Structural determinants of tissue tropism and in vivo pathogenicity for the parvovirus minute virus of mice. J Virol 2005; 79(17):10931-43.
42. Nam H J, Gurda-Whitaker B, Gan W Y, Ilaria S, McKenna R, Mehta P, et al. Identification of the sialic acid structures recognized by minute virus of mice and the role of binding affinity in virulence adaptation. J Biol Chem 2006; 281(35):25670-7.
43. Hemminki A, Belousova N, Zinn K R, Liu B, Wang M, Chaudhuri T R, et al. An adenovirus with enhanced infectivity mediates molecular chemotherapy of ovarian cancer cells and allows imaging of gene expression. Mol Ther 2001; 4(3):223-31.
44. Witlox A M, Van Beusechem V W, Molenaar B, Bras H, Schaap G R, Alemany R, et al. Conditionally replicative adenovirus with tropism expanded towards integrins inhibits osteosarcoma tumor growth in vitro and in vivo. Clin Cancer Res 2004; 10(1 Pt 1):61-7.
45. Burkhart D J, Kalet B T, Coleman M P, Post G C, Koch T H. Doxorubicin-formaldehyde conjugates targeting alphavbeta3 integrin. Mol Cancer Ther 2004; 3(12):1593-604.
46. Sarkioja M, Kanerva A, Salo J, Kangasniemi L, Eriksson M, Raki M, et al. Noninvasive imaging for evaluation of the systemic delivery of capsid-modified adenoviruses in an orthotopic model of advanced lung cancer. Cancer 2006; 107(7):1578-88.
47. Hodivala-Dilke K M, Reynolds A R, Reynolds L E. Integrins in angiogenesis: multitalented molecules in a balancing act. Cell Tissue Res 2003; 314(1):131-44.
48. Assa-Munt N, Jia X, Laakkonen P, Ruoslahti E. Solution structures and integrin binding activities of an RGD peptide with two isomers. Biochemistry 2001; 40(8):2373-8.
49. Nagel H, Maag S, Tassis A, Nestle F O, Greber U F, Hemmi S. The alphavbeta5 integrin of hematopoietic and nonhematopoietic cells is a transduction receptor of RGD-4C fiber-modified adenoviruses. Gene Ther 2003; 10(19):1643-53.
50. Brooks P C, Clark R A, Cheresh D A. Requirement of vascular integrin alpha v beta 3 for angiogenesis. Science 1994; 264(5158):569-71.
51. Zitzmann S, Ehemann V, Schwab M. Arginine-glycine-aspartic acid (RGD)-peptide binds to both tumor and tumor-endothelial cells in vivo. Cancer Res 2002; 62(18):5139-43.
52. Magnusson M K, Hong S S, Henning P, Boulanger P, Lindholm L. Genetic retargeting of adenovirus vectors: functionality of targeting ligands and their influence on virus viability. J Gene Med 2002; 4(4):356-70.
53. Wesseling J G, Bosma P J, Krasnykh V, Kashentseva E A, Blackwell J L, Reynolds P N, et al. Improved gene transfer efficiency to primary and established human pancreatic carcinoma target cells via epidermal growth factor receptor and integrin-targeted adenoviral vectors. Gene Ther 2001; 8(13):969-76.
54. Niu G, Xiong Z, Cheng Z, Cai W, Gambhir S S, Xing L, et al. In vivo bioluminescence tumor imaging of RGD peptide-modified adenoviral vector encoding firefly luciferase reporter gene. Mol Imaging Biol 2007; 9(3):126-34.

55. Piao Y, Jiang H, Alemany R, Krasnykh V, Marini F C, Xu J, et al. Oncolytic adenovirus retargeted to Delta-EGFR induces selective antiglioma activity. Cancer Gene Ther 2009; 16(3):256-65.
56. Laskowski R A, Moss D S, Thornton J M. Main-chain bond lengths and bond angles in protein structures. J Mol Biol 1993; 231(4):1049-67.
57. Hooft R W, Vriend G, Sander C, Abola E E. Errors in protein structures. Nature 1996; 381(6580):272.
58. Colovos C, Yeates T O. Verification of protein structures: patterns of nonbonded atomic interactions. Protein Sci 1993; 2(9):1511-9.
59. Luthy R, Bowie J U, Eisenberg D. Assessment of protein models with three-dimensional profiles. Nature 1992; 356 (6364):83-5.
60. Pontius J, Richelle J, Wodak S J. Deviations from standard atomic volumes as a quality measure for protein crystal structures. J Mol Biol 1996; 264(1):121-36.
61. DeLano W L. The PyMOL Molecular Graphics System. In. San Carlos, Calif., USA: DeLano Scientific LLC.
62. Kestler J, Neeb B, Struyf S, Van Damme J, Cotmore S F, D'Abramo A, et al. cis requirements for the efficient production of recombinant DNA vectors based on autonomous parvoviruses. Hum Gene Ther 1999; 10(10):1619-32.
63. Sambrook J, Russell D W. In Vitro Mutagenesis Using Double-stranded DNA Templates: Selection of Mutants with DpnI. In: Molecular Cloning. 3rd Edition ed. Cold Spring Harbor, N.Y., USA: Cold Spring Harbor Laboratory Press; 2001.
64. Koivunen E, Wang B, Ruoslahti E. Phage libraries displaying cyclic peptides with different ring sizes: ligand specificities of the RGD-directed integrins. Biotechnology (N Y) 1995; 13(3):265-70.
65. Ho S N, Hunt H D, Horton R M, Pullen J K, Pease L R. Site-directed mutagenesis by overlap extension using the polymerase chain reaction. Gene 1989; 77(1):51-9.
66. Reed S E, Staley E M, Mayginnes J P, Pintel D J, Tullis G E. Transfection of mammalian cells using linear polyethylenimine is a simple and effective means of producing recombinant adeno-associated virus vectors. J Virol Methods 2006; 138(1-2):85-98.
67. Zolotukhin S, Byrne B J, Mason E, Zolotukhin I, Potter M, Chesnut K, et al. Recombinant adeno-associated virus purification using novel methods improves infectious titer and yield. Gene Ther 1999; 6(6):973-85.
68. El-Andaloussi N, Endele M, Leuchs B, Bonifati S, Kleinschmidt J, Rommelaere J, et al. Novel adenovirus-based helper system to support production of recombinant parvovirus. Cancer Gene Ther 2011; 18(4):240-9.
69. Chapman M S, Agbandje-Mc Kenna M. Atomic structure of viral particles. London, United Kindom: Hodder Arnold; 2006.
70. Alonso M M, Jiang H, Yokoyama T, Xu J, Bekele N B, Lang F F, et al. Delta-24-RGD in combination with RAD001 induces enhanced anti-glioma effect via autophagic cell death. Mol Ther 2008; 16(3):487-93.
71. Volk A L, Rivera A A, Kanerva A, Bauerschmitz G, Dmitriev I, Nettelbeck D M, et al. Enhanced adenovirus infection of melanoma cells by fiber-modification: incorporation of RGD peptide or Ad5/3 chimerism. Cancer Biol Ther 2003; 2(5):511-5.

The invention claimed is:

1. An H-1 rat parvovirus (H-1PV) comprising a mutation in the polypeptide sequence of the VP proteins, wherein the mutation is at one of or both positions corresponding to I367 and H373 of H-1PV VP2 protein.

2. The H-1 rat parvovirus according to claim 1, wherein the mutation is an I367S mutation.

3. The H-1 rat parvovirus according to claim 1, wherein the mutation is an H373R mutation.

4. The H-1 rat parvovirus according to claim 1, wherein the parvovirus further comprises a foreign peptide or protein with high-affinity for a receptor expressed in a tumor cell.

5. The H-1 rat parvovirus according to claim 4, wherein the foreign peptide or protein comprises the amino acid sequence RGD.

6. The H-1 rat parvovirus according to claim 4, wherein the foreign peptide or protein is inserted at position A 441 of the VP2 protein (corresponding to A583 of the VP1 protein) of the parvovirus.

7. A pharmaceutical composition containing the H-1 rat parvovirus according to claim 1.

8. A method for treating cancer in a human, comprising the step of administering to a human the H-1 rat parvovirus according to claim 1.

9. The method according to claim 8, wherein the cancer is a melanoma, a brain tumor, mammary carcinoma or cervical carcinoma.

10. The method according to claim 8, wherein the cancer is a glioblastoma.

* * * * *

SEQUENCE LISTING

```
<160> NUMBER OF SEQ ID NOS: 14

<210> SEQ ID NO 1
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /mol_type="protein"
      /note="RGD-4C peptide"
      /organism="artificial sequences"

<400> SEQUENCE: 1

Cys Asp Cys Arg Gly Asp Cys Phe Cys
1               5

<210> SEQ ID NO 2
<211> LENGTH: 27
<212> TYPE: DNA
<213> ORGANISM: artificial sequences
<220> FEATURE:
<221> NAME/KEY: source
<222> LOCATION: 1..27
<223> OTHER INFORMATION: /mol_type="DNA"
      /note="oligonucleotide"
      /organism="artificial sequences"

<400> SEQUENCE: 2
agcttatcga taccgtcgac gttaacc                                              27

<210> SEQ ID NO 3
<211> LENGTH: 27
<212> TYPE: DNA
```

```
<213> ORGANISM: artificial sequences
<220> FEATURE:
<221> NAME/KEY: source
<222> LOCATION: 1..27
<223> OTHER INFORMATION: /mol_type="DNA"
      /note="oligonucleotide"
      /organism="artificial sequences"

<400> SEQUENCE: 3
tcgaggttaa cgtcgacggt atcgata                                    27

<210> SEQ ID NO 4
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="primer for clone pVPsub I367S"
      /organism="artificial sequences"

<400> SEQUENCE: 4
ggtaccgcta gacagcacag ctggcgagg                                  29

<210> SEQ ID NO 5
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="primer"
      /organism="artificial sequences"

<400> SEQUENCE: 5
cctcgccagc tgtgctgtct agcggtacc                                  29

<210> SEQ ID NO 6
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="primer pVPsub H373R"
      /organism="artificial sequences"

<400> SEQUENCE: 6
gctggcgagg accgtgatgc aaacggagc                                  29

<210> SEQ ID NO 7
<211> LENGTH: 29
<212> TYPE: DNA
<213> ORGANISM: artificial sequences
<220> FEATURE:
<221> NAME/KEY: source
<222> LOCATION: 1..29
<223> OTHER INFORMATION: /mol_type="DNA"
      /note="primer H373R"
      /organism="artificial sequences"

<400> SEQUENCE: 7
gctccgtttg catcacggtc ctcgccagc                                  29

<210> SEQ ID NO 8
<211> LENGTH: 37
```

```
<212> TYPE: DNA
<213> ORGANISM: artificial sequences
<220> FEATURE:
<221> NAME/KEY: source
<222> LOCATION: 1..37
<223> OTHER INFORMATION: /mol_type="DNA"
      /note="primer RGD1"
      /organism="artificial sequences"

<400> SEQUENCE: 8
gccgcggaga ctgtttctgc ggcagaacta acatgca                              37

<210> SEQ ID NO 9
<211> LENGTH: 39
<212> TYPE: DNA
<213> ORGANISM: artificial sequences
<220> FEATURE:
<221> NAME/KEY: source
<222> LOCATION: 1..39
<223> OTHER INFORMATION: /mol_type="DNA"
      /note="primer RGD2"
      /organism="artificial sequences"

<400> SEQUENCE: 9
aacagtctcc gcggcagtca caagctatgg cgtcttctc                            39

<210> SEQ ID NO 10
<211> LENGTH: 17
<212> TYPE: DNA
<213> ORGANISM: artificial sequences
<220> FEATURE:
<221> NAME/KEY: source
<222> LOCATION: 1..17
<223> OTHER INFORMATION: /mol_type="DNA"
      /note="primer External 1"
      /organism="artificial sequences"

<400> SEQUENCE: 10
cgaagattgg gccaaac                                                    17

<210> SEQ ID NO 11
<211> LENGTH: 18
<212> TYPE: DNA
<213> ORGANISM: artificial sequences
<220> FEATURE:
<221> NAME/KEY: source
<222> LOCATION: 1..18
<223> OTHER INFORMATION: /mol_type="DNA"
      /note="primer External 2"
      /organism="artificial sequences"

<400> SEQUENCE: 11
tttgtcccaa atttgtcc                                                   18

<210> SEQ ID NO 12
<211> LENGTH: 17
<212> TYPE: DNA
<213> ORGANISM: artificial sequences
<220> FEATURE:
<221> NAME/KEY: source
<222> LOCATION: 1..17
<223> OTHER INFORMATION: /mol_type="DNA"
      /note="TaqMan probe"
      /organism="artificial sequences"

<400> SEQUENCE: 12
atgcagccag acagtta                                                    17

<210> SEQ ID NO 13
```

```
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="primer NS1-FOR"
      /organism="artificial sequences"

<400> SEQUENCE: 13
gcgcggcaga attcaaact                                                    19

<210> SEQ ID NO 14
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer NS1-REV"
      /organism="artificial sequences"

<400> SEQUENCE: 14
ccacctggtt gagccatcat                                                   20
```